United States Patent
Lathia et al.

(10) Patent No.: US 11,136,368 B2
(45) Date of Patent: Oct. 5, 2021

(54) CANCER TREATMENT USING CX26 BLOCKING PEPTIDES

(71) Applicant: THE CLEVELAND CLINIC FOUNDATION, Cleveland, OH (US)

(72) Inventors: Justin D. Lathia, Cleveland, OH (US); Ofer Reizes, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 16/326,741

(22) PCT Filed: Aug. 23, 2017

(86) PCT No.: PCT/US2017/048134
§ 371 (c)(1),
(2) Date: Feb. 20, 2019

(87) PCT Pub. No.: WO2018/039302
PCT Pub. Date: Mar. 1, 2018

(65) Prior Publication Data
US 2019/0352367 A1    Nov. 21, 2019

Related U.S. Application Data

(60) Provisional application No. 62/378,346, filed on Aug. 23, 2016.

(51) Int. Cl.
| C07K 14/705 | (2006.01) |
| A61P 35/00 | (2006.01) |
| A61K 38/00 | (2006.01) |

(52) U.S. Cl.
CPC ............ *C07K 14/705* (2013.01); *A61P 35/00* (2018.01); *A61K 38/00* (2013.01)

(58) Field of Classification Search
None
See application file for complete search history.

(56) References Cited

U.S. PATENT DOCUMENTS

| 6,759,046 B1 * | 7/2004 | Gaudernack ............ A61P 35/00 424/184.1 |
| 7,786,074 B2 * | 8/2010 | Gourdie ................. A61K 38/07 514/1.2 |

FOREIGN PATENT DOCUMENTS

| WO | 2006/069181 A2 | 6/2006 |
| WO | 2006/134494 A2 | 12/2006 |
| WO | 2009/097077 A2 | 8/2009 |

OTHER PUBLICATIONS

UniProtKB—P29033 last updated Feb. 26, 2020 (Year: 2020).*
Helmer et al. "Peptides and Peptide Analogs to Inhibit Protein-Protein Interactions" in T. Böldicke (ed.), Protein Targeting Compounds, Advances in Experimental Medicine and Biology, 2016, pp. 147-183 (Year: 2006).*
Laird and Lampe "Therapeutic strategies targeting connexins," Nature Reviews Drug Discovery, 2018, vol. 17, pp. 905-921 (Year: 2018).*
Aasen, Trond, et al. "Gap junctions and cancer: communicating for 50 years." Nature Reviews Cancer 16.12 (2016): 775.
Akrap, Nina, et al. "Identification of distinct breast cancer stem cell populations based on single-cell analyses of functionally enriched stem and progenitor pools." Stem cell reports 6.1 (2016): 121-136.
Al-Hajj, Muhammad, et al. "Prospective identification of tumorigenic breast cancer cells." Proceedings of the National Academy of Sciences 100.7 (2003): 3983-3988.
Bogoyevitch, Marie A., et al. "Taking the cell by stealth or storm? Protein transduction domains (PTDs) as versatile vectors for delivery." DNA and cell biology 21.12 (2002): 879-894.
Bry, Céline, et al. "Loss of connexin 26 in mammary epithelium during early but not during late pregnancy results in unscheduled apoptosis and impaired development." Developmental biology 267.2 (2004): 418-429.
Cronier, Laurent, et al. "Gap junctions and cancer: new functions for an old story." Antioxidants & redox signaling 11.2 (2009): 323-338.
Coligan, J. E., et al. "Current Protocols in Immunology Wiley, New York." (2001).
Ezumi, Koji, et al. "Aberrant expression of connexin 26 is associated with lung metastasis of colorectal cancer." Clinical Cancer Research 14.3 (2008): 677-684.
Fischer, Peter M., Eberhard Krausz, and David P. Lane. "Cellular delivery of impermeable effector molecules in the form of conjugates with peptides capable of mediating membrane translocation." Bioconjugate chemistry 12.6 (2001): 825-841.
Garcia-Echeverria, C., and Stephan Ruetz. "β-homolysine oligomers: A new class of trojan carriers." Bioorganic & medicinal chemistry letters 13.2 (2003): 247-251.
Ginestier, Christophe, et al. "ALDH1 is a marker of normal and malignant human mammary stem cells and a predictor of poor clinical outcome." Cell stem cell 1.5 (2007): 555-567.
M Golubovskaya, Vita. "FAK and Nanog cross talk with p53 in cancer stem cells." Anti-Cancer Agents in Medicinal Chemistry (Formerly Current Medicinal Chemistry—Anti-Cancer Agents) 13.4 (2013): 576-580.
Greenberg, N. M., et al. "Prostate cancer in a transgenic mouse." Proceedings of the National Academy of Sciences 92.8 (1995): 3439-3443.
Hao, Huifang, et al. "Focal adhesion kinase as potential target for cancer therapy." Oncology reports 22.5 (2009): 973-979.
Heathcote, Kirsten, et al. "A connexin 26 mutation causes a syndrome of sensorineural hearing loss and palmoplantar hyperkeratosis (MIM 148350)." Journal of medical genetics 37.1 (2000): 50-51.

(Continued)

*Primary Examiner* — Christina Bradley
(74) *Attorney, Agent, or Firm* — Tarolli, Sundheim, Covell & Tummino LLP

(57) ABSTRACT

Blocking peptides that inhibit FAK or NANOG binding to Cx26, and a method of treating cancer by administering these blocking peptides to a subject in need thereof are described.

6 Claims, 8 Drawing Sheets

Specification includes a Sequence Listing.

(56) References Cited

OTHER PUBLICATIONS

Hirschi, Karen K., et al. "Gap junction genes Cx26 and Cx43 individually suppress the cancer phenotype of human mammary carcinoma cells and restore differentiation potential." Cell Growth and Differentiation—Publication American Association for Cancer Research 7.7 (1996): 861-870.
Hitomi, Masahiro, et al. "Differential connexin function enhances self-renewal in glioblastoma." Cell reports 11.7 (2015): 1031-1042.
Ho, Baotran, et al. "Nanog increases focal adhesion kinase (FAK) promoter activity and expression and directly binds to FAK protein to be phosphorylated." Journal of Biological Chemistry 287.22 (2012): 18656-18673.
Hu, Yifang, and Gordon K. Smyth. "ELDA: extreme limiting dilution analysis for comparing depleted and enriched populations in stem cell and other assays." Journal of immunological methods 347.1-2 (2009): 70-78.
Janssen-Timmen, U., et al. "Reduced number of gap junctions in rat hepatocarcinomas detected by monoclonal antibody." Carcinogenesis 7.9 (1986): 1475-1482.
Jiang, Jean X., and Sumin Gu. "Gap junction-and hemichannel-independent actions of connexins." Biochimica et Biophysica Acta (BBA)—Biomembranes 1711.2 (2005): 208-214.
Kanczuga-Koda, L., et al. "Increased expression of connexins 26 and 43 in lymph node metastases of breast cancer." Journal of clinical pathology 59.4 (2006): 429-433.
Lathia, Justin D., et al. "Integrin alpha 6 regulates glioblastoma stem cells." Cell stem cell 6.5 (2010): 421-432.
Lathia, Justin D., et al. "High-throughput flow cytometry screening reveals a role for junctional adhesion molecule a as a cancer stem cell maintenance factor." Cell reports 6.1 (2014): 117-129.
Leifert, Jens A., and J. Lindsay Whitton. ""Translocatory proteins" and "protein transduction domains": a critical analysis of their biological effects and the underlying mechanisms." Molecular Therapy 8.1 (2003): 13-20.
Lindsay, Mark A. "Peptide-mediated cell delivery: application in protein target validation." Current opinion in pharmacology 2.5 (2002): 587-594.
Low, Jennifer A., and Frederic J. de Sauvage. "Clinical experience with Hedgehog pathway inhibitors." Journal of Clinical Oncology 28.36 (2010): 5321-5326.
Luo, Ming, et al. "Mammary epithelial-specific ablation of the focal adhesion kinase suppresses mammary tumorigenesis by affecting mammary cancer stem/progenitor cells." Cancer research 69.2 (2009): 466-474.
Machida, Keigo. "Existence of cancer stem cells in hepatocellular carcinoma: myth or reality?." Hepatology international 11.2 (2017): 143-147.
Maeda, Shoji, et al. "Structure of the connexin 26 gap junction channel at 3.5 Å resolution." Nature 458.7238 (2009): 597.
Maestrini, Elena, et al. "A missense mutation in connexin26, D66H, causes mutilating keratoderma with sensorineural deafness (Vohwinkel's syndrome) in three unrelated families." Human molecular genetics 8.7 (1999): 1237-1243.
Matteucci, Mark Douglas, and M. Ho Caruthers. "Synthesis of deoxyoligonucleotides on a polymer support." Journal of the American Chemical Society 103.11 (1981): 3185-3191.
McLachlan, Elizabeth, Qing Shao, and Dale W. Laird. "Connexins and gap junctions in mammary gland development and breast cancer progression." Journal of Membrane Biology 218.1-3 (2007): 107-121.
Mesnil, Marc. "Connexins and cancer." Biology of the Cell 94.7-8 (2002): 493-500.
Merrifield, Robert B. "Solid phase peptide synthesis. I. The synthesis of a tetrapeptide." Journal of the American Chemical Society 85.14 (1963): 2149-2154.

Naoi, Yasuto, et al. "Connexin26 expression is associated with lymphatic vessel invasion and poor prognosis in human breast cancer." Breast cancer research and treatment 106.1 (2007): 11-17.
Naus, Christian C., and Dale W. Laird. "Implications and challenges of connexin connections to cancer." Nature reviews Cancer 10.6 (2010): 435.
Hill, Robert L., and Hans Neurath. The Proteins. 3rd ed., vol. 4, Academic Press, 1979.
PCT International Search Report and Written Opinion for corresponding Application Serial No. PCT/US2017/048134, dated Nov. 20, 2017, pp. 1-14.
Bodanszky, Miklos. Principles of Peptide Synthesis. Springer Verlag, 1984.
Polin, Lisa, et al. "Treatment of human prostate tumors PC-3 and TSU-PR1 with standard and investigational agents in SCID mice." Investigational new drugs 15.2 (1997): 99-108.
Mcomie, J. Protective Groups in Organic Chemistry. Springer, 2012.
Qin, Hong, et al. "Retroviral delivery of connexin genes to human breast tumor cells inhibits in vivo tumor growth by a mechanism that is independent of significant gap junctional intercellular communication." Journal of Biological Chemistry 277.32 (2002): 29132-29138.
Qin, Hong, et al. "Connexin26 regulates the expression of angiogenesis-related genes in human breast tumor cells by both GJIC-dependent and-independent mechanisms." Cell communication & adhesion 10.4-6 (2003): 387-393.
Sambrook, J., et al. Molecular Cloning: a Laboratory Manual. 2nd ed., Cold Spring Harbor Laboratory Press, 1989.
Sheridan, Cormac. "Genentech obtains proof of concept for hedgehog inhibition." (2009): 968.
Stewart, Michael Kg, et al. "Cx26 knockout predisposes the mammary gland to primary mammary tumors in a DMBA-induced mouse model of breast cancer." Oncotarget 6.35 (2015): 37185.
Stewart, Michael Kg, et al. "Mammary gland specific knockdown of the physiological surge in Cx26 during lactation retains normal mammary gland development and function." PloS one 9.7 (2014): e101546.
Tate, Amanda W., et al. "Changes in gap junctional connexin isoforms during prostate cancer progression." The Prostate 66.1 (2006): 19-31.
Thiagrajan, Praveena S., et al. "Development of a Fluorescent Reporter System to Delineate Cancer Stem Cells in Triple-Negative Breast Cancer." Stem Cells 33.7 (2015): 2114-2125.
Thomas, Tamsin, Debra Telford, and Dale W. Laird. "Functional domain mapping and selective trans-dominant effects exhibited by Cx26 disease-causing mutations." Journal of Biological Chemistry 279.18 (2004): 19157-19168.
Tung, Ching-Hsuan, and Ralph Weissleder. "Arginine containing peptides as delivery vectors." Advanced drug delivery reviews 55.2 (2003): 281-294.
Valiente, Manuel, et al. "Focal adhesion kinase modulates radial glia-dependent neuronal migration through connexin-26." Journal of Neuroscience 31.32 (2011): 11678-11691.
Vinken, Mathieu, et al. "Non-channel functions of connexins in cell growth and cell death." Biochimica et Biophysica Acta (BBA)—Biomembranes 1818.8 (2012): 2002-2008.
Wilgenbus, Klaus K., et al. "Expression of Cx26, Cx32 and Cx43 gap junction proteins in normal and neoplastic human tissues." International journal of cancer 51.4 (1992): 522-529.
Xie, Xiujie, et al. "Phosphorylation of Nanog is essential to regulate Bmi1 and promote tumorigenesis." Oncogene 33.16 (2014): 2040.
Zhao, Jihe, and Jun-Lin Guan. "Signal transduction by focal adhesion kinase in cancer." Cancer and Metastasis Reviews 28.1-2 (2009): 35-49.

* cited by examiner

A CONNEXIN EXPRESSION IN TNBC TISSUE RELATIVE TO NORMAL BREAST TISSUE
(2408 TNBC AND 250 NORMAL BREAST SAMPLES)

B Cx26 EXPRESSION IN TNBC CSC MODELS

C

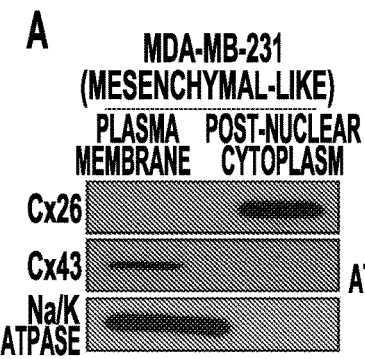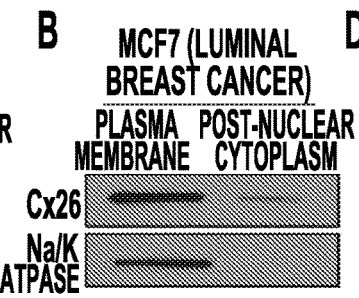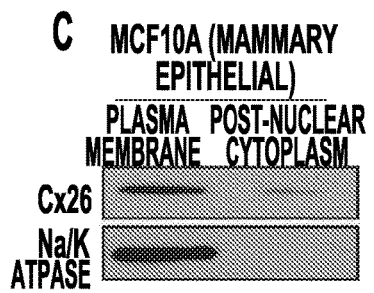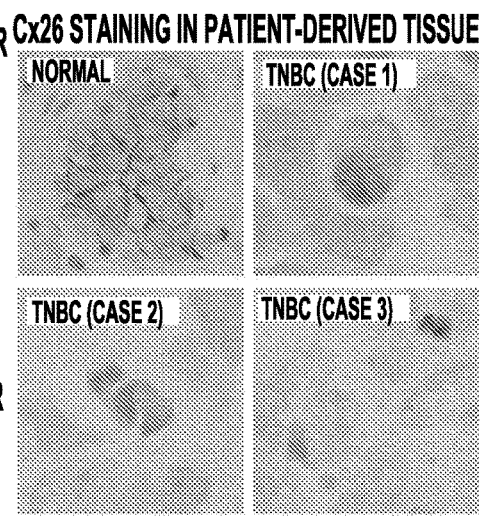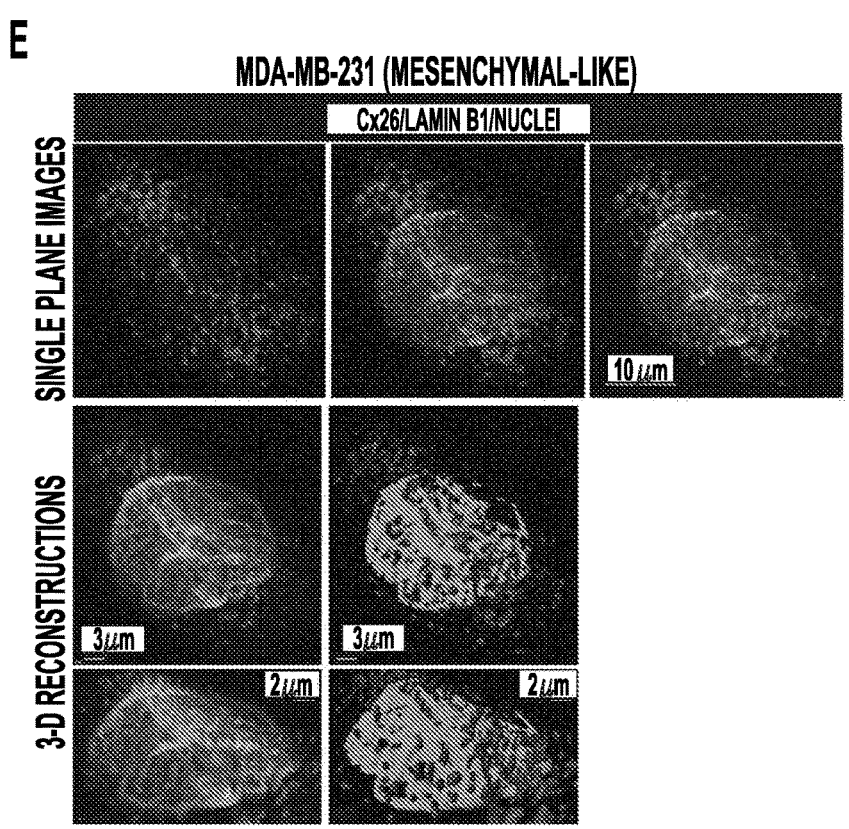
FIG. 4A
FIG. 4B
FIG. 4C
FIG. 4D
FIG. 4E

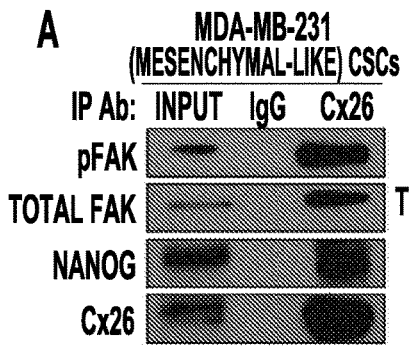
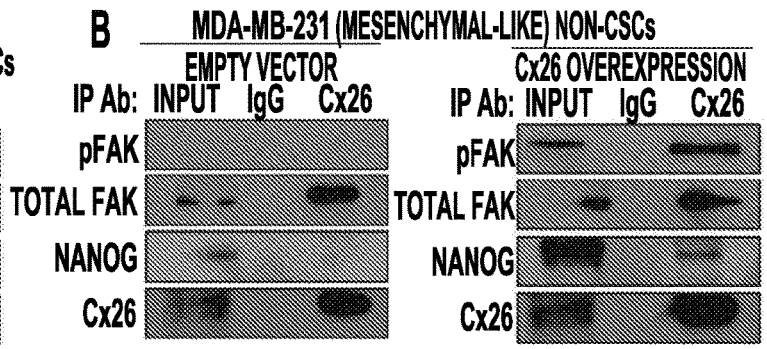
FIG. 6A
FIG. 6B
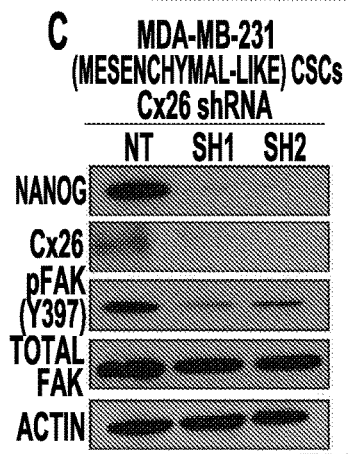
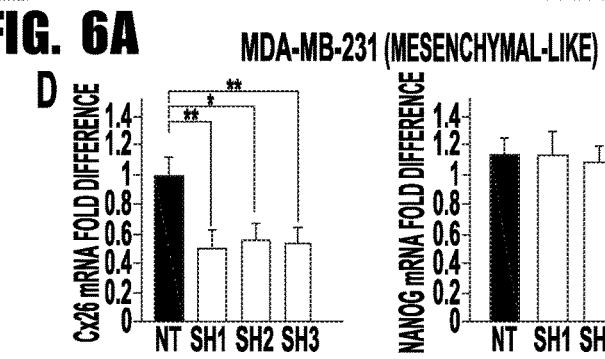
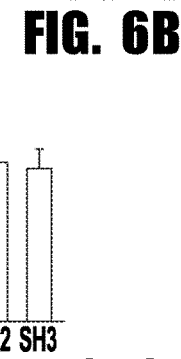
FIG. 6C
FIG. 6D
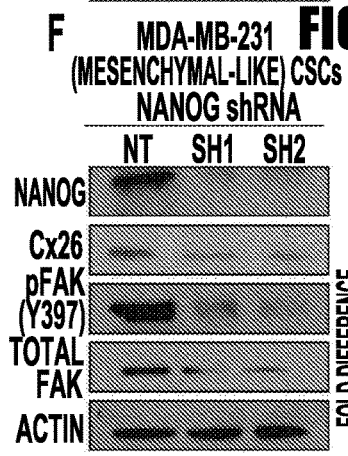
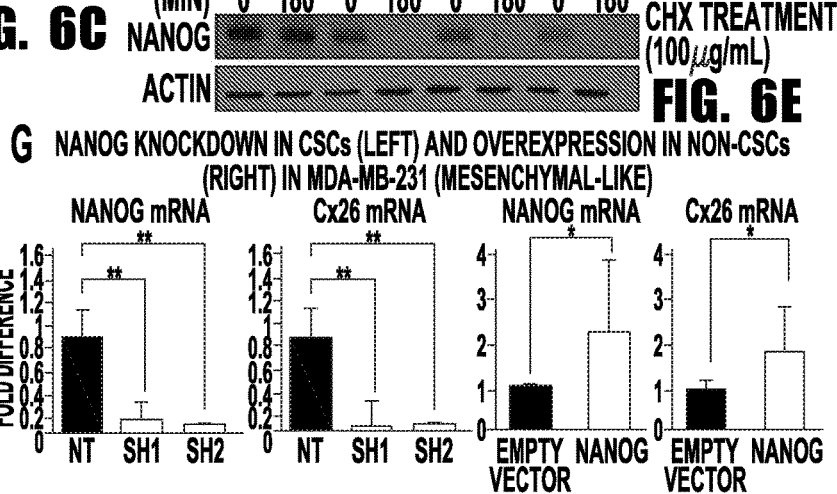
FIG. 6E
FIG. 6F
FIG. 6G
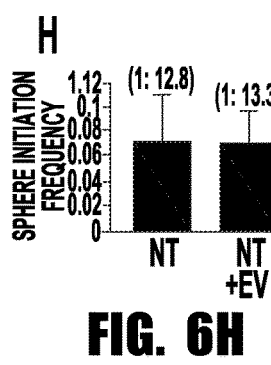
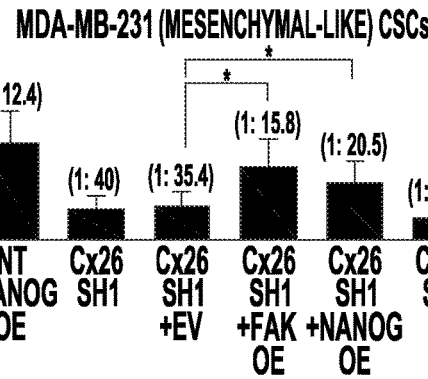
FIG. 6H

SEQUENCE LISTING

```
<160> NUMBER OF SEQ ID NOS: 30

<210> SEQ ID NO 1
<211> LENGTH: 20
<212> TYPE: PRT
<213> ORGANISM: Artificial Sequence
<220> FEATURE:
<223> OTHER INFORMATION: Cx26 peptide fragment

<400> SEQUENCE: 1

Met Asp Trp Gly Thr Leu Gln Thr Ile Leu Gly Gly Val Asn Lys His
1               5                   10                  15

Ser Thr Ser Ile
            20

<210> SEQ ID NO 2
<211> LENGTH: 35
<212> TYPE: PRT
<213> ORGANISM: Artificial Sequence
<220> FEATURE:
<223> OTHER INFORMATION: Cx26 blocking peptide

<400> SEQUENCE: 2

Lys Glu Val Trp Gly Asp Glu Gln Ala Asp Phe Val Cys Asn Thr Leu
1               5                   10                  15

Gln Pro Gly Cys Lys Asn Val Cys Tyr Asp His Tyr Phe Pro Ile Ser
            20                  25                  30

His Ile Arg
        35

<210> SEQ ID NO 3
<211> LENGTH: 33
<212> TYPE: PRT
<213> ORGANISM: Artificial Sequence
<220> FEATURE:
<223> OTHER INFORMATION: Cx26 peptide fragment

<400> SEQUENCE: 3

Arg His Glu Lys Lys Arg Lys Phe Ile Lys Gly Glu Ile Lys Ser Glu
1               5                   10                  15

Phe Lys Asp Ile Glu Glu Ile Lys Thr Gln Lys Val Arg Ile Glu Gly
            20                  25                  30

Ser
```

```
<210> SEQ ID NO 4
<211> LENGTH: 38
<212> TYPE: PRT
<213> ORGANISM: Artificial Sequence
<220> FEATURE:
<223> OTHER INFORMATION: Cx26 peptide fragment

<400> SEQUENCE: 4

Tyr Val Met Tyr Asp Gly Phe Ser Met Gln Arg Leu Val Lys Cys Asn
1               5                   10                  15

Ala Trp Pro Cys Pro Asn Thr Val Asp Cys Phe Val Ser Arg Pro Thr
            20                  25                  30

Glu Lys Thr Val Phe Thr
        35

<210> SEQ ID NO 5
<211> LENGTH: 11
<212> TYPE: PRT
<213> ORGANISM: Artificial Sequence
<220> FEATURE:
<223> OTHER INFORMATION: Cx26 peptide fragment

<400> SEQUENCE: 5

Arg Tyr Cys Ser Gly Lys Ser Lys Lys Pro Val
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 6

Met Asp Trp Gly Thr Leu Gln Thr Ile Leu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 7

Gly Gly Val Asn Lys His Ser Thr Ser Ile
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 8

Lys Glu Val Trp Gly Asp Glu Gln Ala Asp
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 9
```

```
Phe Val Cys Asn Thr Leu Gln Pro Gly Cys
1               5                   10
```

<210> SEQ ID NO 10
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 10

```
Leu Gln Pro Gly Cys Lys Asn Val Cys Tyr
1               5                   10
```

<210> SEQ ID NO 11
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 11

```
Asp His Tyr Phe Pro Ile Ser His Ile Arg
1               5                   10
```

<210> SEQ ID NO 12
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 12

```
Arg His Glu Lys Lys Arg Lys Phe Ile Lys
1               5                   10
```

<210> SEQ ID NO 13
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 13

```
Gly Glu Ile Lys Ser Glu Phe Lys Asp Ile
1               5                   10
```

<210> SEQ ID NO 14
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 14

```
Lys Ser Glu Phe Lys Asp Ile Glu Glu Ile
1               5                   10
```

<210> SEQ ID NO 15
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 15

```
Lys Thr Gln Lys Val Arg Ile Glu Gly Ser
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 16

Tyr Val Met Tyr Asp Gly Phe Ser Met Gln
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 17

Arg Leu Val Lys Cys Asn Ala Trp Pro Cys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 18

Pro Cys Pro Asn Thr Val Asp Cys Phe Val
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Cx26 peptide fragment

<400> SEQUENCE: 19

Ser Arg Pro Thr Glu Lys Thr Val Phe Thr
1               5                   10

<210> SEQ ID NO 20
<211> LENGTH: 6
<212> TYPE: PRT
<213> ORGANISM: Artificial Sequence
<220> FEATURE:
<223> OTHER INFORMATION: Cx26 peptide fragment

<400> SEQUENCE: 20

Arg Tyr Cys Ser Gly Lys
1               5

<210> SEQ ID NO 21
<211> LENGTH: 6
<212> TYPE: PRT
<213> ORGANISM: Artificial Sequence
<220> FEATURE:
<223> OTHER INFORMATION: Cx26 peptide fragment

<400> SEQUENCE: 21

Lys Ser Lys Lys Pro Val
```

```
1               5

<210> SEQ ID NO 22
<211> LENGTH: 13
<212> TYPE: PRT
<213> ORGANISM: Artificial Sequence
<220> FEATURE:
<223> OTHER INFORMATION: protein transduction domain

<400> SEQUENCE: 22

Gly Arg Lys Lys Arg Arg Gln Arg Arg Arg Pro Pro Gln
1               5                   10

<210> SEQ ID NO 23
<211> LENGTH: 16
<212> TYPE: PRT
<213> ORGANISM: Artificial Sequence
<220> FEATURE:
<223> OTHER INFORMATION: protein transduction domain

<400> SEQUENCE: 23

Arg Gln Ile Lys Ile Trp Phe Gln Asn Arg Arg Met Lys Trp Lys Lys
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: protein transduction domain

<400> SEQUENCE: 24

Arg Arg Met Lys Trp Lys Lys
1               5

<210> SEQ ID NO 25
<211> LENGTH: 18
<212> TYPE: PRT
<213> ORGANISM: Artificial Sequence
<220> FEATURE:
<223> OTHER INFORMATION: protein transduction domain

<400> SEQUENCE: 25

Arg Gly Gly Arg Leu Ser Tyr Ser Arg Arg Phe Ser Thr Ser Thr
1               5                   10                  15

Gly Arg

<210> SEQ ID NO 26
<211> LENGTH: 10
<212> TYPE: PRT
<213> ORGANISM: Artificial Sequence
<220> FEATURE:
<223> OTHER INFORMATION: protein transduction domain

<400> SEQUENCE: 26

Arg Arg Leu Ser Tyr Ser Arg Arg Arg Phe
1               5                   10

<210> SEQ ID NO 27
<211> LENGTH: 17
<212> TYPE: PRT
<213> ORGANISM: Artificial Sequence
<220> FEATURE:
<223> OTHER INFORMATION: protein transduction domain

<400> SEQUENCE: 27
```

```
Arg Gly Gly Arg Leu Ala Tyr Leu Arg Arg Trp Ala Val Leu Gly
1               5                   10                  15

Arg

<210> SEQ ID NO 28
<211> LENGTH: 8
<212> TYPE: PRT
<213> ORGANISM: Artificial Sequence
<220> FEATURE:
<223> OTHER INFORMATION: protein transduction domain

<400> SEQUENCE: 28

Arg Arg Arg Arg Arg Arg Arg Arg
1               5

<210> SEQ ID NO 29
<211> LENGTH: 51
<212> TYPE: PRT
<213> ORGANISM: Artificial Sequence
<220> FEATURE:
<223> OTHER INFORMATION: synthetic peptide

<400> SEQUENCE: 29

Arg Gln Ile Lys Ile Trp Phe Gln Asn Arg Arg Met Lys Trp Lys Lys
1               5                   10                  15

Lys Glu Val Trp Gly Asp Glu Gln Ala Asp Phe Val Cys Asn Thr Leu
            20                  25                  30

Gln Pro Gly Cys Lys Asn Val Cys Tyr Asp His Tyr Phe Pro Ile Ser
        35                  40                  45

His Ile Arg
    50

<210> SEQ ID NO 30
<211> LENGTH: 54
<212> TYPE: PRT
<213> ORGANISM: Artificial Sequence
<220> FEATURE:
<223> OTHER INFORMATION: synthetic peptide

<400> SEQUENCE: 30

Arg Gln Ile Lys Ile Trp Phe Gln Asn Arg Arg Met Lys Trp Lys Lys
1               5                   10                  15

Tyr Val Met Tyr Asp Gly Phe Ser Met Gln Arg Leu Val Lys Cys Asn
            20                  25                  30

Ala Trp Pro Cys Pro Asn Thr Val Asp Cys Phe Val Ser Arg Pro Thr
        35                  40                  45

Glu Lys Thr Val Phe Thr
    50
```

CANCER TREATMENT USING CX26 BLOCKING PEPTIDES

CONTINUING APPLICATION DATA

This application claims the benefit of U.S. Provisional Application Ser. No. 62/378,346, filed Aug. 23, 2016, which is incorporated by reference herein.

GOVERNMENT FUNDING

This invention was made with government support under CA191263 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 21, 2017, is named Cx26 blocking peptides_ST25 and is 7,979 bytes in size.

BACKGROUND

Breast cancer remains the leading cause of cancer-related deaths among women worldwide despite advances in screening, diagnosis, and treatment. The inter-patient heterogeneity of breast cancer has long been recognized, and molecular genetic approaches have revealed distinct subgroups that are associated with different overall patient outcomes. Among these subgroups, triple-negative breast cancer (TNBC), which is defined by the lack of estrogen receptor (ER), progesterone receptor (PR), and Her2/neu receptor expression has the poorest prognosis and accounts for 15-20% of all breast cancer cases. In TNBC, intratumoral heterogeneity has emerged as a hallmark of the malignant state and accounts for persistent tumor growth, therapeutic resistance, and metastasis. These phenotypes are largely driven by a self-renewing population of cancer stem cells (CSCs). Al-Hajj M. et al., Proc Natl Acad Sci U S A., 100(7):3983-8 (2003). The molecular mechanisms of CSC self-renewal are the focus of intensive study as they are likely to yield next-generation therapeutic strategies, as exemplified by the current clinical evaluation of the first generation of anti-CSC therapies. Low, J. A. et al., J Clin Oncol 28, 5321-5326 (2010); Sheridan, C., Nat Biotechnol 27, 968-969 (2009).

Attempts to elucidate the complexity of CSC maintenance have focused on intrinsic driver mutations and altered developmental signaling pathways. Magee, J. A., et al., Cancer Cell 21, 283-296 (2012). The elevated cellular density within tumors stimulates cellular programs that are activated by cell-cell contact and close proximity. The gap junction (GJ) family of proteins composed of connexin subunits canonically function in GJ plaques at the interface of adjacent cells to facilitate direct cell-cell communication. Connexins can also function non-canonically as single membrane channels (hemichannels) or as signaling hubs adjacent to any organelle and/or the plasma membrane. Stewart, M. K. et al., Oncotarget 6, 37185-37199 (2015). In the context of cancer, the role of connexins as tumor suppressors has been widely described in many cancer models. Cronier, L. et al., Antioxid Redox Signal 11, 323-338 (2009); Mesnil, M., Biol Cell 94, 493-500 (2002). However, the paradigm that connexins have a global tumor-suppressive role has been challenged by evidence that connexins are pro-tumorigenic and facilitate tumor progression and metastasis. Ezumi, K. et al., Clin Cancer Res 14, 677-684 (2008); Aasen, T. et al., Nat Rev Cancer 16, 775-788 (2016).

In the breast, Cx26 and Cx43 are the connexin subunits involved in maintaining homeostasis during the development and in the physiological function of the mammary gland (McLachlan, E. et al., J. Membr Biol 218, 107-121 (2007)) and in breast cancer, connexins have been described to be both pro-and anti-tumorigenic by regulating transformation, proliferation, cell survival, and metastasis. Most studies to date suggest a tumor-suppressive role for Cx26 in early breast cancer progression based on evidence that Cx26 is frequently absent or down-regulated in human breast cancer cell lines and human primary tumors. Hirschi, K. K. et al., Cell Growth Differ 7, 861-870 (1996); Kanczuga-Koda, L. et al., J Clin Pathol 59, 429-433 (2006). However, clinical observations demonstrate a strong correlation between poor overall survival and increased Cx26 expression in breast cancer tissue samples harvested following treatments (chemotherapy/surgery) and decreased overall survival. Moreover, Cx26 expression has been shown to be associated with increased lymphatic vessel invasion, tumor size, and poor prognosis in human breast cancers. Naoi, Y. et al., Breast Cancer Res Treat 106, 11-17 (2007).

SUMMARY

Tumors adapt their phenotypes during growth and in response to therapies through dynamic changes in cellular processes. The connexin family proteins enable such dynamic changes during development and their dysregulation leads to disease states. The cellular networks formed by connexins have been reported to exhibit tumor-suppressive functions, including in triple-negative breast cancer (TNBC). However, the inventors found that connexin 26 (Cx26) is elevated in self-renewing cancer stem cells (CSCs) and is necessary and sufficient for their maintenance. Cx26 exerts its self-renewal promoting function by forming a signaling complex with a pluripotency transcription factor NANOG and focal adhesion kinase (FAK) resulting in NANOG stabilization and FAK activation in TNBC. This ternary complex is not formed in mammary epithelial or luminal breast cancer cells. These findings challenge the paradigm that connexins are tumor suppressors in TNBC and reveal a unique function for Cx26 in regulating the core self-renewal signaling that controls CSC maintenance.

BRIEF DESCRIPTION OF THE FIGURES

FIGS. 4A-4E provide graphs and images showing the nuclear and cytoplasmic localization of Cx26 in MDA-MB-231 cells. (A) The cytosol and organelle fraction and the plasma membrane fraction of MDA-MB-231 parental cells were probed for a plasma membrane marker (sodium potassium ATPase), Cx26 and Cx43 proteins by immunoblotting. (B, C) Cx26 localization in MCF7 and MCF10A cells was determined by immunoblotting of the plasma membrane and the cytosol and organelle fractions with Na/K ATPase blot as an indicator of plasma membrane fraction quality. (D) Immunohistochemistry micrographs demonstrate the staining pattern of Cx26 (brown) in normal and adjacent TNBC tissue from 3 patients. Nuclei were counterstained in blue. Images provided at 400×. (E) Confocal micrographs of MDA-MB-231 TNBC cells stained with antibodies against Cx26 (red) and lamin B1 (green). Single plane images and 3-D reconstructions of areas were generated in Imaris Corresponding fluorescent images are provided on top of 3-D reconstructions. Nuclei were counterstained with Hoechst 33342, and scale bars are provided on each micrograph and reconstruction.

FIGS. 6A-6H provide graphs and images showing that Cx26/NANOG/FAK interaction is enriched in the MDA-MB-231 CSCs and Cx26 regulates NANOG stability. (A) Immunoprecipitation with Cx26 antibody was performed in MDA-MB-231 CSCs and (B) non-CSCs transduced with either empty vector or Cx26-overexpression vector. The precipitates were probed for pFAK (Y397), total FAK, NANOG and Cx26 by immunoblotting. (C) Immunoblots of the cell lysates of MDA-MB-231 NANOG-GFP CSCs silenced for Cx26 using two shRNA constructs each (sh1 and sh2) and a non-targeting (NT) control were probed with Cx26, NANOG, pFAK (Y397), and total FAK antibodies. Actin was used as a loading control. (D) Fold difference in mRNA expression of Cx26 and NANOG in Cx26-silenced MDA-MB-231 CSCs compared with NT control was determined by qPCR. Actin was used as a normalization control. (E) Cx26-silenced and non-targeting control (NT) MDA-MB-231 CSCs were treated with cycloheximide (CHX) to block de novo protein synthesis. Cells were harvested at 0 and 180 minutes following cycloheximide treatment and probed for NANOG expression by immunoblotting. Actin was used as a loading control. (F) Immunoblots of MDA-MB-231 NANOG-GFP CSCs silenced for NANOG using two shRNA constructs each and a non-targeting control were probed with Cx26, NANOG, pFAK (Y397), and total FAK antibodies. Actin was used as a loading control. (G) Fold difference in mRNA expression of Cx26 and NANOG in NANOG-silenced MDA-MB-231 CSCs and NANOG-overexpressed MDA-MB-231 non-CSCs compared with their corresponding controls was determined by qPCR. Actin was used as a normalization control. (H) Stem cell frequencies of Cx26-silenced MDA-MB-231 CSCs overexpressing FAK or NANOG compared with NT and/or empty vector controls were determined by limiting dilution sphere-forming assays.

DETAILED DESCRIPTION

Figure 1A:
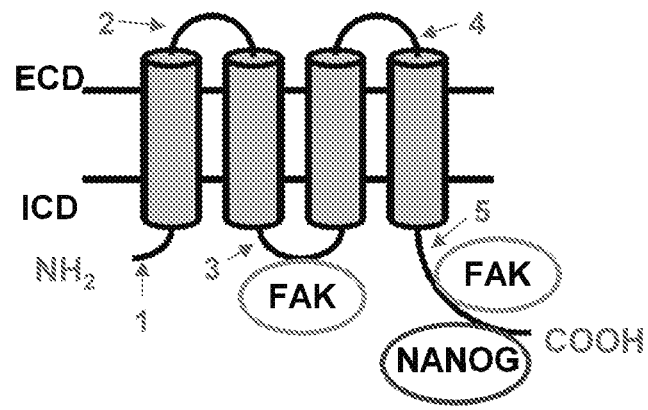
FIGS. 1A and 1B provide graphs and images showing the interaction between FAK and NANOG with the intracellular domains of Cx26; Schematic depiction of the binding of FAK and NANOG with Cx26 (A) and example SPR plots (B) of FAK and NANOG binding with the cytoplasmic tail of Cx26. Cx26 peptides assessed at a range from 1 nM to 100 µM and compared to buffer control.
Figure 1B:
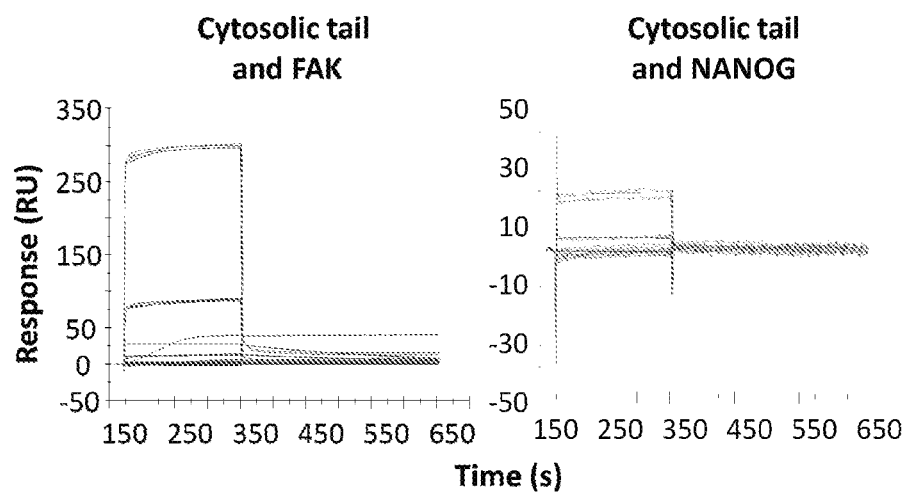

Unless otherwise defined, all technical and scientific terms used herein have the same meaning as commonly understood by one of ordinary skill in the art to which this application pertains. Although methods and materials similar or equivalent to those described herein can be used in the practice or testing of the exemplary embodiments, suitable methods and materials are described below. In case of conflict, the present specification, including definitions, will control. In addition, the materials, methods, and examples are illustrative only and not intended to be limiting.

The terminology as set forth herein is for description of the embodiments only and should not be construed as limiting the application as a whole. Unless otherwise specified, "a," "an," "the," and "at least one" are used interchangeably. Furthermore, as used in the description of the application and the appended claims, the singular forms "a", "an", and "the" are inclusive of their plural forms, unless contraindicated by the context surrounding such. Furthermore, the recitation of numerical ranges by endpoints includes all of the numbers subsumed within that range (e.g., 1 to 5 includes 1, 1.5, 2, 2.75, 3, 3.80, 4, 5, etc.).

"Amino acid" is used herein to refer to a chemical compound with the general formula: $NH_2$—CRH—COOH, where R, the side chain, is H or an organic group. Where R is organic, R can vary and is either polar or nonpolar (i.e., hydrophobic). The following abbreviations are used throughout the application: A=Ala=Alanine, T=Thr=Threonine, V=Val=Valine, C=Cys=Cysteine, L=Leu=Leucine, Y=Tyr=Tyrosine, I=Ile=Isoleucine, N=Asn=Asparagine, P=Pro=Proline, Q=Gln=Glutamine, F=Phe=Phenylalanine, D=Asp=Aspartic Acid, W=Trp=Tryptophan, E=Glu=Glutamic Acid, M=Met=Methionine, K=Lys=Lysine, G=Gly=Glycine, R=Arg=Arginine, S=Ser=Serine, H=His=Histidine. Unless otherwise indicated, the term "amino acid" as used herein also includes amino acid derivatives that nonetheless retain the general formula.

As used herein, the term "polynucleotide" refers to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, siRNAs, microRNAs, and ribonucleoproteins. The term also encompasses nucleic acids, i.e., oligonucleotides, containing known analogues of natural nucleotides, as well as nucleic acid-like structures with synthetic backbones.

The term "isolated" means that the material is removed from its original environment (e.g., the natural environment if it is naturally occurring) or is synthetically derived. For example, a naturally-occurring polypeptide present in a living animal is not isolated, but the same polypeptide, separated from some or all of the coexisting materials in the natural system, is isolated. Such a polypeptide could be part of a composition, and still be isolated in the composition, and not be a part of its natural environment.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc. Treatment also includes partial or total destruction or differentiation of the undesirable proliferating cells with minimal effects on normal cells. In accordance with the present invention, desired mechanisms of treatment at the cellular level include stimulation of differentiation in cancer and pre-cancer cells.

As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those having an enhanced risk of developing precancers and cancers. An elevated risk represents an above-average risk that a subject will develop cancer, which can be determined, for example, through family history or the detection of genes causing a predisposition to developing cancer.

"Pharmaceutically acceptable" as used herein means that the compound or composition is suitable for administration to a subject to achieve the treatments described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses. An effective amount, on the other hand, is an amount sufficient to provide a significant chemical effect, such as the inhibition of cancer growth by a detectable amount.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human.

Blocking Peptides

In one aspect, the present invention provides blocking peptides. The blocking peptides are a fragment of the Cx26 protein, comprising an amino acid sequence substantially similar to at least a portion of the amino acid sequence of an intracellular or extracellular domain of Cx26.

The term "blocking peptide," as used herein, refers to peptides that can interfere with the binding of FAK or NANOG to Cx26, thereby interfering with or "blocking" the formation of the Cx26/NANOG/FAK complex. Blocking formation of the Cx26/NANOG/FAK complex, as the phrase is used herein, refers to a decrease in the formation of the complex relative to what would be seen in the absence of blocking peptides, and does not require that 100% of formation be blocked. The interaction between Cx26, NONOG, and FAK is shown in FIG. 1A. The Cx26/NANOG/FAK complex is a gap junction that facilitates communication between cancer cells, and therefore inhibition of formation of the complex blocks the self-renewal and viability of cancer cells, and in particular cancer stem cells. The blocking peptides are substantially similar to a portion of an intracellular or extracellular domain region of Cx26. As shown in FIG. 1A, the beta sheet regions of Cx26 are imbedded in the cell membrane, while the intracellular and extracellular domain regions (e.g., the N-terminus, extracellular loops, intracellular loops, and C-terminus regions) are exposed either to the exterior or the interior of the cell. As a result of the similarity of the blocking peptides to portions of Cx26, the blocking peptides associate with the corresponding (i.e., binding) portions of NANOG or FAK, thereby blocking the association of NANOG or FAK with Cx26.

The blocking peptides competitively inhibit binding of Cx26 with FAK and NANOG. By competitive inhibition, it is meant that the blocking peptides "competing" with the binding of the natural substrate (i.e., either FAK or NANOG). Depending on the amount of blocking peptide present, the inhibition can either be essentially complete (i.e., about 100%) or partial (i.e., any percentage less than 100%, such as 90% or 50%). It is known that there is substantial homology between Cx26 of other mammalian species, and blocking peptides based on these other sequences are also encompassed by the invention.

The structure and identity of the Focal Adhesion Kinase (FAK), Nanog transcription factor (NANOG), and Connexin 26 (Cx26) proteins are known to those skilled in the art. Focal Adhesion Kinase is a 125-kDa non-receptor and non-membrane associated protein tyrosine kinase, containing three main domains: a centrally located catalytic kinase domain, flanked by a large N-terminal domain comprising the FERM region, and a C-terminal domain harboring the focal adhesion targeting region. See Hao et al., Oncol Rep., 22(5):973-9 (2009). Human Nanog protein consist of 305 amino acids, which are divided into an N-terminal (amino acids 1-95), homeobox domain (amino acids 96-155), and C-terminal (amino acids 156-305) regions. See Misui et al., Cell, 113(5); 631-642 (2003). Connexin 26 is a gap junction channel that contains four trans-membrane helices with the C- and N-terminal domains located in the intracellular region. The cytoplasmic end of the hemichannel is positively charged and the transmembrane end is negatively charged. Connexin 26 forms a hemichannels via a hexamer of connexin 26 subunits that forms a functional channel with a hemichannel on an adjacent cell. See Maeda et al., Nature, 458(7238):597-602 (2009).

The invention includes blocking peptides that are substantially similar to at least a portion of the amino acid sequence of an extracellular domain of Cx26. The term "a portion," as used herein, refers to an amino acid sequence within the extracellular domains of Cx26 that includes at least 4 amino acids. In further embodiments, a portion refers to an amino acid sequence that is at least 6 amino acids in length, an amino acid sequence that is at least 8 amino acids in length, or an amino acid sequence that is at least 10 amino acids in length. The blocking peptides therefore consist of at least 4, 6, 8, or 10 amino acids. Likewise, the blocking peptides described herein can have a maximum size. The maximum size of the blocking peptide relates to the overall size of the peptide, and includes any additional sequences linked to the peptide, such as a protein transduction domain. In some embodiments, the blocking peptide has a maximum size of less than about 200 amino acids, while in other embodiments the blocking peptide has a maximum size of less than about 100 amino acids. In other embodiments, the blocking peptide has a maximum size of 75 amino acids or less, 50 amino acids or less, 40 amino acids or less, 30 amino acids or less, or 20 amino acids or less.

As used herein, the term "polypeptide" refers to an oligopeptide, peptide, or protein sequence, or to a fragment, portion, or subunit of any of these, and to naturally occurring or synthetic molecules. The term "polypeptide" also includes amino acids joined to each other by peptide bonds or modified peptide bonds, i.e., peptide isosteres, and may contain any type of modified amino acids. The term "polypeptide" also includes peptides and polypeptide fragments, motifs and the like, glycosylated polypeptides, all "mimetic" and "peptidomimetic" polypeptide forms, and retro-inversion peptides (also referred to as all-D-retro or retro-enantio peptides).

"Substantially similar" means that a given amino acid (or nucleic acid) sequence shares at least 85%, more preferably at least 90%, and even more preferably at least 95% identity with a reference sequence. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Substantially similar peptides include those that differ by one or more amino acid alterations, where the alterations, e.g., substitutions, additions or deletions of amino acid residues, do not abolish the properties of the relevant peptides, such as their ability to associate with FAK or NANOG. Furthermore, only sequences describing or encoding proteins in which only conservative substitutions are made in the conserved regions are substantially similar overall. Preferable, substantially similar sequences also retain the distinctive activity of the polypeptide.

Examples of conservative substitutions include the substitution of a non-polar (hydrophobic) residue such as isoleucine, valine, leucine or methionine for another. Likewise, the present invention contemplates the substitution of one polar (hydrophilic) residue such as between arginine and lysine, between glutamine and asparagine, and between glycine and serine. Additionally, the substitution of a basic residue such as lysine, arginine or histidine for another or the substitution of one acidic residue such as aspartic acid or glutamic acid for another is also contemplated. Examples of non-conservative substitutions include the substitution of a non-polar (hydrophobic) residue such as isoleucine, valine, leucine, alanine, methionine for a polar (hydrophilic) residues such as cysteine, glutamine, glutamic acid, lysine and/or a polar residue for a non-polar residue.

The phrase "conservative substitution" also includes the use of chemically derivatized residues in place of non-derivatized residues as long as the peptide retains the requisite ability to associate with FAK or NANOG. Substantially similar peptides also include the presence of additional amino acids or the deletion of one or more amino acids which do not affect the requisite ability to associate with FAK or NANOG. For example, substantially similar peptides can contain an N- or C-terminal cysteine, by which, if desired, the peptide may be covalently attached to a carrier protein, e.g., albumin Such attachment can decrease clearing of the peptide from the blood and also decrease the rate of proteolysis of the peptides. In addition, for purposes of the present invention, peptides containing D-amino acids in place of L-amino acids are also included in the term "conservative substitution." The presence of such D-isomers can help minimize proteolytic activity and clearing of the peptide.

Studies by the inventors have shown that some amino acids are particular important for the interaction between Cx26 and the other two peptides involved in gap junction formation, FAK and NANOG. Table 1 provides a summary of FAK and NANOG dissociation constants with Cx26 intracellular domains. Accordingly, in some embodiments, the blocking peptide includes specific amino acid sequences within the extracellular and intracellular domains of Cx26. The standard amino acids and their one and three letter abbreviations are known to those skilled in the art. Examples of suitable blocking peptides are shown in Table 2, which provides the peptide sequences associated with intracellular and extracellular domains of the Cx26 protein, including the extracellular (ECD) and intracellular domains (ICD) shown in FIG. 1A. Accordingly, in some embodiments, the blocking peptide comprises an amino acid sequence substantially similar to at least a portion of an amino acid sequence selected from the group consisting of SEQ ID NO: 1, SEQ ID NO: 2, SEQ ID NO: 3, SEQ ID NO: 4, and SEQ ID NO: 5.

TABLE 1

FAK and NANOG dissociation constants

| Analyte | Ligand | Dissociation constant (KD) |
|---|---|---|
| Intracellular loop (peptide 3) | FAK | $1.131^{-5}$ M |
| C-terminus (peptide 5) | FAK | $1.49^{-5}$ M |
| C-terminus (peptide 5) | NANOG | $1.7^{-7}$ M |

TABLE 2

Cx26 blocking peptides

| Peptide Number | Location | Sequence |
|---|---|---|
| 1 | N-terminus | MDWGTLQTILGGVNKHSTSI (SEQ ID NO: 1) |
| 2 | Extracellular loop 1 | KEVWGDEQADFVCNTLQPGC KNVCYDHYFPISHIR (SEQ ID NO: 2) |
| 3 | Intracellular loop | RHEKKRKFIKGEIKSEFKDI EEIKTQKVRIEGS (SEQ ID NO: 3) |
| 4 | Extracellular loop 2 | YVMYDGFSMQRLVKCNAWPC PNTVDCFVSRPTEKTVFT (SEQ ID NO: 4) |
| 5 | C-terminus | RYCSGKSKKPV (SEQ ID NO: 5) |

Blocking peptides also include peptides comprising a sequence consisting of only a portion of the amino acids present in one of the sequences found in the intracellular or extracellular domains of Cx26. The portion of amino acids remain in the sequence found in the original sequence, but include fewer amino acids than the entire sequence. Portions of the amino acids include 6, 7, 8, 9, 10, 11, 12, 13, 14, 15, 16, 17, 18, 19 or 20 amino acids. These blocking peptides can have a maximum size corresponding to any of the maximum sizes described herein for blocking peptides. For example, in some embodiments, the blocking peptides including only a portion of SEQ ID NO 1-5 can include 50 or fewer amino acids.

In some embodiments, the blocking peptide comprises a sequence consisting of 10 amino acids present in SEQ ID NO: 1. Examples of such sequences include MDWGTLQTIL (SEQ ID NO: 6) and GGVNKHSTSI (SEQ ID NO: 7).

In some embodiments, the blocking peptide comprises a sequence consisting of 10 amino acids present in SEQ ID NO: 2. Examples of such sequences include KEVWGDEQAD (SEQ ID NO: 8), FVCNTLQPGC (SEQ ID NO: 9), LQPGCKNVCY (SEQ ID NO: 10) and DHYFPISHIR (SEQ ID NO: 11).

In some embodiments, the blocking peptide comprises a sequence consisting of 10 amino acids present in SEQ ID NO: 3. Examples of such sequences include RHEKKRKFIK (SEQ ID NO: 12); GEIKSEFKDI (SEQ ID NO: 13); KSEFKDIEEI (SEQ ID NO: 14), and KTQKVRIEGS (SEQ ID NO: 15).

In some embodiments, the blocking peptide comprises a sequence consisting of 10 amino acids present in SEQ ID NO: 4. Examples of such sequences include YVMYDGFSMQ (SEQ ID NO: 16), RLVKCNAWPC (SEQ ID NO: 17), PCPNTVDCFV (SEQ ID NO: 18), and SRPTEKTVFT (SEQ ID NO: 19).

In some embodiments the blocking peptide comprises a sequence consisting of 6 amino acids present in SEQ ID NO: 5. Examples of such sequences include RYCSGK (SEQ ID NO: 20) and KSKKPV (SEQ ID NO: 21)

Preparation of Blocking Peptides

The blocking peptides of the present invention, and homologs, analogs and fragments thereof, may be synthesized by a number of known techniques. For example, the peptides may be prepared using the solid-phase synthetic technique initially described by Merrifield in J. Am. Chem. Soc. 85:2149 2154 (1963). In general, the method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine. Other peptide synthesis techniques may be found in M. Bodanszky, et al. Peptide Synthesis, John Wiley & Sons, 2d Ed., (1976) and other references readily available to those skilled in the art. A summary of polypeptide synthesis techniques can be found in J. Stuart and J. D. Young, Solid Phase Peptide Synthesis, Pierce Chemical Company, Rockford, Ill., (1984). Peptides may also be synthesized by solution methods as described in The Proteins, Vol. II. 3d Ed., Neurath, H. et al., Eds., p. 105 237, Academic Press, New York, N.Y. (1976). Appropriate protective groups for use in different peptide syntheses are described in the above-mentioned texts as well as in J. F. W. McOmie, Protective Groups in Organic Chemistry, Plenum Press, New York, N.Y. (1973). The peptides of the present invention can also be prepared by chemical or enzymatic cleavage from the entire or larger portions of the Cx26 molecule.

A preferred method of solid phase peptide synthesis entails attaching the protected or derivatized amino acid to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino carboxyl group is then removed from this newly added amino acid residue, and the next amino acid (suitably protected) is then added, and so forth. After all the desired amino acids have been linked in the proper sequence, any remaining terminal and side group protecting groups including the solid support are removed sequentially or concurrently to yield the final peptide. The lyophilized oligopeptides are resuspended in double distilled $H_2O$ at 2 mg/ml as stock solutions and subsequently diluted in M199-HPS for experiments.

Additionally, the peptides of the present invention may also be prepared by recombinant DNA techniques (see e.g. Current Protocols in Molecular Cloning Ausubel et al., 1995, John Wiley & Sons, New York); Sambrook et al., 1989, Molecular Cloning: A Laboratory Manual, Second Edition, Cold Spring Harbor Laboratory Press, New York; Coligan et al. Current Protocols in Immunology, John Wiley & Sons Inc., New York, N.Y. (1994)). The skilled artisan understands that any of a wide variety of expression systems can be used to provide the recombinant peptides of the present invention. The precise host cell used is not critical to the invention. The blocking peptides can be produced in a prokaryotic host (e.g. *E. coli*), or in a eukaryotic host (e.g., *S. cerevisiae* or mammalian cells, e.g. COS1, CHO, NIH3T3, and JEG3 cells, or in the cells of an arthropod, e.g. *S. frugiperda*). Such cells are available from e.g. the American Type Culture Collection, Manassas, Va. The method of transfection and the choice of expression vehicle will depend on the host system selected. Transformation and transfection methods are described, e.g. in Sambrook et al. supra; expression vehicles can be chosen from those provided e.g. in Cloning Vectors: A Laboratory Manual, P. H. Powels et al. (1985), Supp. 1987.

For most of the amino acids used to build proteins, more than one coding nucleotide triplet (codon) can code for a particular amino acid residue. This property of the genetic code is known as redundancy. Therefore, a number of different nucleotide sequences can code for a particular subject blocking peptide. In some embodiments, a deoxyribonucleic acid (DNA) molecule or segment that defines a gene coding for, i.e., capable of expressing, a subject peptide or a subject chimeric peptide from which a peptide of the present invention can be enzymatically or chemically cleaved can be used.

DNA molecules that encode peptides of the present invention can be synthesized by chemical techniques, for example, the phosphotriester method of Matteuccie, et al., J. Am. Chem. Soc. 103:3185 (1981). Using a chemical DNA synthesis technique, desired modifications in the peptide sequence can be made by making substitutions for bases which code for the native amino acid sequence. Ribonucleic acid equivalents of the above described DNA molecules may also be used.

A nucleic acid molecule comprising a vector capable of replication and expression of a DNA molecule defining coding sequence for a subject polypeptide or subject chimeric polypeptide is also contemplated.

Protein Transduction Domains

The present invention includes blocking peptides comprising a fragment of Cx26 that are capable of inhibiting the binding of FAK or NANOG to Cx26. In some embodiments, the blocking peptides are cell-permeable peptides. Cell-permeable blocking peptides are peptides that are able to overcome the cell membrane barrier and enter a cell to interfere with FAK or NANOG binding to Cx26. A preferred method of enhancing cell permeation by blocking peptides is the use of a protein transduction domain (PTD). PTDs can be conjugated to a blocking peptide to facilitate cell-permeation by the blocking peptide. PTDs are heterogeneous in size and lack sequence homology, although most share a positive charge and are amphipathic. The PTDs of the present invention are those that facilitate intracellular transport. In certain embodiments, PTDs can be antimicrobial peptides such as protegrin 1, Bactenecin 7, Buforin, and Maginin; a host of arginine-rich RNA- and DNA-binding peptides (e.g., HIV-1 trans activating protein (TAT) and Drosophila homeodomain transcription factor *Antennapedia* (a.k.a. Penetratin); chimeric PTDs such as Transportan; lysine- and arginine-rich peptides derived from phage-display libraries; polyarginine; and most recently, β-homolysine oligomers (See, Fisher et al., Bioconjugate Chemistry 12: 825-841 (2001); Lindsay, Current Opinions in Pharmacology 2: 587-594 (2002); Tung et al., Advanced Drug Delivery Reviews 55: 281-294 (2003); Leifert et al., Molecular Therapy 8: 13-19 (2003); Bogoyevitch et al., DNA and Cell Biology 21: 879-894 (2002); Garcia-Echeverria et al., Bioorganic & Medicinal Chemistry Letters 13: 247-251 (2003), incorporated herein by reference in their entireties). In certain embodiments, the PTDs are addition, reverso-, retro-inverso, and enantio-forms of many of the PTDs described herein.

Examples of specific PTD conjugates suitable for use with a blocking peptide include the following PTD sequences, as well as sequences that are substantially similar to these sequences. GRKKRRQRRRPPQ (SEQ ID NO: 22); RQIKIWFQNRRMKWKK (SEQ ID NO: 23); RRMKWKK (SEQ. ID. NO. 24); RGGRLSYSRRRFSTSTGR (SEQ. ID. NO. 25); RRLSYSRRRF (SEQ. ID. NO. 26); RGGRLAY-LRRRWAVLGR (SEQ. ID. NO. 27); and RRRRRRRR (SEQ. ID. NO. 28). The PTD conjugates can be directly linked to the blocking peptide, or a number of intervening linking peptides can be included between the blocking peptide and the PTD. For example, from 1-10 intervening linking peptides can be included. Examples of blocking peptides that are directly conjugated to a PTD are provided by a peptide obtained from extracellular loop— RQIKIWFQNRRMKWKK KEVWGD-EQADFVCNTLQPGCKNVCYDHYFPISHIR (SEQ ID NO: 29) and a peptide obtained from extracellular loop 2—RQIKIWFQNRRMKWKK YVMYDGFSMQRLVKCNAWPCPNTVDCFVSRPT-EKTVFT (SEQ ID NO: 30).

In some embodiments, the blocking peptide can be conjugated to a protein transduction domain that is derived from *Antennapedia*. The PTD can alternatively include all or part of the *Drosophila Antennapedia* (Antp) homeodomain (HD) protein. For example, the PTD may comprise the third helix of Antp-HD, which has cell penetration properties. The region responsible for translocation in Antp-HD has been localized to amino acids 43-58 (i.e., the third helix), a 16 amino acid-long peptide rich in basic amino acids. The third helix has the amino acid sequence RQIKIWFQNRRMKWKK (SEQ ID NO: 23). This polypeptide has been used to direct biologically active substances to the cytoplasm and nucleus of cells in culture. Accordingly, the PTD conjugated to a blocking peptide the present invention may comprise an Antp-HD polypeptide, an Antp-HD homolog, an Antp-HD variant, and/or an Antp-HD fragment, such as a fragment containing the third helix of Antp-HD, for example.

Protein transduction domains can be linked to the other amino acids of the blocking peptide by chemical cross-linking or by other techniques known to those skilled in the art, such as recombinant techniques. For example, a PTD can be fused to an amino acid sequence that is substantially similar to at least a portion of an extracellular domain of Cx26 by expression in a suitable eukaryotic or prokaryotic host cell. The fused protein can be expressed by introducing a cDNA sequence encoding the fused protein together with an N-terminal leader sequence (e.g., a 6-histidine tag) to enable purification of the expressed cell-permeable blocking peptide. Alternately, the blocking peptide based on the Cx26 fragment can include a linker sequence that operably couples the PTD with the amino acids of the blocking peptide.

While any of the PTDs (including domains and/or sequences and/or fragments thereof exhibiting membrane translocation activity) provided above may be used for the purpose of generating a cell-permeable polypeptide, it should be appreciated that other variations are also possible. For example, variations such as mutations (e.g., point mutations, deletions, insertions, etc.) of any of the sequences disclosed herein may be employed, provided that some membrane translocation activity is retained. Furthermore, it will be appreciated that homologs of PTDs from any other organism, including those of synthetic origin, may also be used.

Cancer Treatment

In one aspect, the present invention provides a method of treating or preventing cancer in a subject in need thereof. The method includes administering to the subject a therapeutically effective amount of a blocking peptide that inhibits FAK or NANOG binding to Cx26.

The blocking peptide can be any of the blocking peptides described herein. For example, in some embodiments, the blocking peptide comprises an amino acid sequence substantially similar to at least a portion of an intracellular or extracellular domain of Cx26, while in other embodiments the blocking peptide consists of 50 amino acids or less. In further embodiments, the blocking peptide that is administered to the subject comprises an amino acid sequence that is substantially similar to at least a portion of an amino acid sequence selected from the group consisting of SEQ ID NO: 1, SEQ ID NO: 2, SEQ ID NO: 3, SEQ ID NO: 4, and SEQ ID NO: 5. In additional embodiments, the blocking peptide further comprises a protein transduction domain.

The blocking peptides can be used to treat or prevent the development of cancer. Cells become cancerous when they lose their ability to stop dividing, to attach to other cells, to stay where they belong, and to die at the proper time. Cancer is generally initiated by an environmental insult or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as precancerous cells. Normal cells will commit cell suicide (programmed cell death) when they are no longer needed. Until then, they are protected from cell suicide by several protein clusters and pathways. One of the protective pathways is the PI3K/AKT pathway; another is the RAS/MEK/ERK pathway. Sometimes the genes along these protective pathways are mutated in a way that turns them permanently "on", rendering the cell incapable of committing suicide when it is no longer needed, which can be an important step in cancer development.

Cancer results in an increased number of cancer cells in a subject. These cells may form an abnormal mass of cells called a tumor, the cells of which are referred to as tumor cells. The overall amount of tumor cells in the body of a subject is referred to as the tumor load. Tumors can be either benign or malignant. A benign tumor contains cells that are proliferating but remain at a specific site and are often encapsulated. The cells of a malignant tumor, on the other hand, can invade and destroy nearby tissue and spread to other parts of the body through a process referred to as metastasis. In many forms of treatment-resistant cancer, a self-renewing population of cancer stem cells (CSCs) plays an important role.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Examples of types of cancer that can be treated using the compounds of the present invention include cancer is selected from the group consisting of bladder cancer, prostate cancer, liver cancer, breast cancer, colon cancer, and leukemia. The role of connexins as tumor suppressors has been widely described in many cancer models. Cronier, L. et al., Antioxid Redox Signal 11, 323-338 (2009); Mesnil, M., Biol Cell 94, 493-500 (2002).

In some embodiments, the cancer being treated is breast cancer. Breast cancer is cancer that develops from breast tissue. Breast cancer most commonly develops in cells from the lining of milk ducts and the lobules that supply the ducts with milk. Cancers developing from the ducts are known as ductal carcinomas, while those developing from lobules are known as lobular carcinomas. In addition, there are more than 18 other sub-types of breast cancer. Breast cancer is often first detected by detection of a lump or a mammogram, which can be followed by imaging by ultrasound or MRI when necessary. Most types of breast cancer are easy to diagnose by microscopic analysis of a biopsy of the affected area of the breast. In some situations, a core biopsy or vacuum-assisted breast biopsy is obtained. Risk factors for developing breast cancer include being female, obesity, lack of physical exercise, drinking alcohol, hormone replacement therapy during menopause, ionizing radiation, early age at first menstruation, having children late or not at all, older age, and family history. About 5-10% of breast cancer cases are due to genes inherited from a person's parents, including the BRCA1 and BRCA2 genes.

In some embodiments, the breast cancer being treated is triple negative breast cancer. Triple negative breast cancer is Triple negative breast cancers are estrogen receptor-negative (ER-negative), progesterone receptor-negative, and HER2-negative, which makes them more difficult to treat with many types of anticancer treatment.

The blocking peptides of the invention can be used for both prophylactic and therapeutic treatment. When used for cancer treatment, the blocking peptides can be referred to as anticancer, or antitumor agents. The blocking peptides can, for example, be administered prophylactically to a mammal prior to the development of cancer. Prophylactic administration, also referred to as prevention, is effective to decrease the likelihood that cancer will develop in the subject. For prophylactic treatment, the subject is any human or animal subject, and preferably is a human subject who is at risk of acquiring a disorder characterized by unwanted, rapid cell proliferation, such as cancer. The subject may be at risk due to exposure to carcinogenic agents, being genetically predisposed to disorders characterized by unwanted, rapid cell proliferation, and so on.

Alternatively, blocking peptides of the invention can, for example, be administered therapeutically to a subject that already has cancer. For purposes of treatment, a subject at risk includes any human or animal subject who has a disorder characterized by unwanted, rapid cell proliferation. Such disorders include, but are not limited to cancers and precancers. In one embodiment of therapeutic administration, administration of the blocking peptides is effective to eliminate the cancer; in another embodiment, administration of the blocking peptides is effective to decrease the symptoms or spread of the cancer.

The effectiveness of cancer treatment may be measured by evaluating a reduction in tumor load or decrease in tumor growth in a subject in response to the administration of the blocking peptides. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

Candidate peptides may be tested for effectiveness in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate peptides and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate peptides can be used in these animal models to determine if a candidate peptide decreases one or more of the symptoms associated with the cancer, including, for instance, cancer metastasis, cancer cell motility, cancer cell invasiveness, or combinations thereof.

Methods of cancer treatment using the blocking peptides described herein can further include the step of ablating the cancer using methods in addition to administration of a blocking peptide. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, and administration of immunotoxins.

Administration of Blocking Peptides

The peptides of the present invention can be administered acutely (i.e., during the onset or shortly after events leading to inflammation or autoimmune disease), or can be administered prophylactically (e.g., before scheduled surgery, or before the appearance of signs or symptoms), or administered during the course of inflammation or autoimmune disease to reduce or ameliorate the progression of symptoms that would otherwise occur. The timing and interval of administration is varied according to the subject's symptoms, and can be administered at an interval of several hours to several days, over a time course of hours, days, weeks or longer, as would be determined by one skilled in the art.

The compositions containing the blocking peptides are generally administered intravenously. When administered intravenously, the peptide compositions may be combined with other ingredients, such as carriers and/or adjuvants. The peptides may also be covalently attached to a protein carrier, such as albumin, so as to minimize clearing of the peptides. There are no limitations on the nature of the other ingredients, except that such ingredients must be pharmaceutically acceptable, efficacious for their intended administration and cannot degrade the activity of the active ingredients of the compositions. Examples of other ingredients contemplated by the present invention include, but are not limited to chemotherapeutic agents. When employed together with blocking peptides, these agents may be employed in lesser dosages than when used alone.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants or vegetable oils. Sterilization can be accomplished by any art-recognized technique, including but not limited to, filtration or addition of antibacterial or antifungal agents, for example, paraben, chlorobutano, phenol, sorbic acid or thimerosal. Further, isotonic agents such as sugars or sodium chloride may be incorporated in the subject compositions.

Production of sterile injectable solutions containing the subject peptides is accomplished by incorporated these compounds in the required amount in the appropriate solvent with various ingredients enumerated above, as required, followed by sterilization, preferably filter sterilization. To obtain a sterile powder, the above solutions are vacuum-dried or freeze-dried as necessary. The blocking peptides are preferably isolated, as defined herein, before inclusion in a pharmaceutical form such as an injectable solution.

When the peptides of the invention are administered orally, the pharmaceutical compositions thereof containing an effective dose of the peptide can also contain an inert diluent, as assimilable edible carrier and the like, be in hard or soft shell gelatin capsules, be compressed into tablets, or may be in an elixir, suspension, syrup or the like. The subject peptides are thus compounded for convenient and effective administration in pharmaceutically effective amounts with a suitable pharmaceutically acceptable carrier in a therapeutically effective amount.

The expressions "effective amount" or "therapeutically effective amount," as used herein, refers to a sufficient amount of agent to interfere with the interaction between Cx26 and FAK or NANOG, and to exhibit a therapeutic effect. The exact amount required will vary from subject to subject, depending on the species, age, and general condition of the subject, the particular therapeutic agent, its mode and/or route of administration, and the like. It will be understood, however, that the total daily usage of the compounds and compositions of the present invention can be decided by an attending physician within the scope of sound medical judgment. The specific therapeutically effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific composition employed; the duration of the treatment; drugs used in combination or coincidental with the specific composition employed; and like factors well known in the medical arts.

The peptides can be administered in a manner compatible with the dosage formulation and in such amount as well be therapeutically effective. Systemic dosages depend on the age, weight and conditions of the patient and on the administration route. For example, a suitable dose for the administration to adult humans ranges from about 0.001 to about 20.0 mg per kilogram of body weight. The peptides should preferably be administered in an amount of at least about 50 mg per dose, more preferably in an amount up to about 500 mg to about 1 gram per dose. Since the peptide compositions of this invention will eventually be cleared from the bloodstream, re-administration of the compositions is indicated and preferred.

As used herein, a pharmaceutically acceptable carrier includes any and all solvents, dispersion media, coatings, antibacterial and antifungal agents, isotonic agents the like. The use of such media and agents are well-known in the art. The pharmaceutically acceptable carriers used in conjunction with the peptides of the present invention vary according to the mode of administration. For example, the compositions may be formulated in any suitable carrier for oral liquid formulation such as suspensions, elixirs and solutions. Compositions for liquid oral dosage include any of the usual pharmaceutical media such as, for example, water, oils, alcohols, flavoring agents, preservatives, coloring agents and the like. In the case of oral solid preparations (capsules and tablets) carriers such as starches, sugars, diluents, granulating agents, lubricants, binders, disintegrating agents and the like may be used. In addition, carriers such as liposomes and microemulsions may be used.

The following example is included for purposes of illustration and is not intended to limit the scope of the invention.

EXAMPLE

Example 1

Cx26 Drives Self-Renewal in Triple-Negative Breast Cancer Via Interaction with Focal Adhesion Kinase and NANOG While connexin function has been assessed in TNBC, its role in CSCs has yet to be determined. The inventors recently defined a role for Cx46 in CSC maintenance in glioblastoma that opposes the previously described role of Cx43 as a tumor suppressor, suggesting that different connexin family members may play distinct roles. Hitomi, M. et al., Cell reports 11, 1031-1042 (2015). Based on previous work and observations that Cx26, Cx32, Cx40, and Cx43 do not localize to gap junction plaques in breast cancer, it was hypothesized that a subset of connexins may regulate CSC maintenance in TNBC but that these proteins likely function in a non-canonical manner Jiang, J.X. & Gu, S., Biochim Biophys Acta 1711, 208-214 (2005).

Results

Cx26 is expressed in TNBC tissue and CSCs.

Figure 2A:
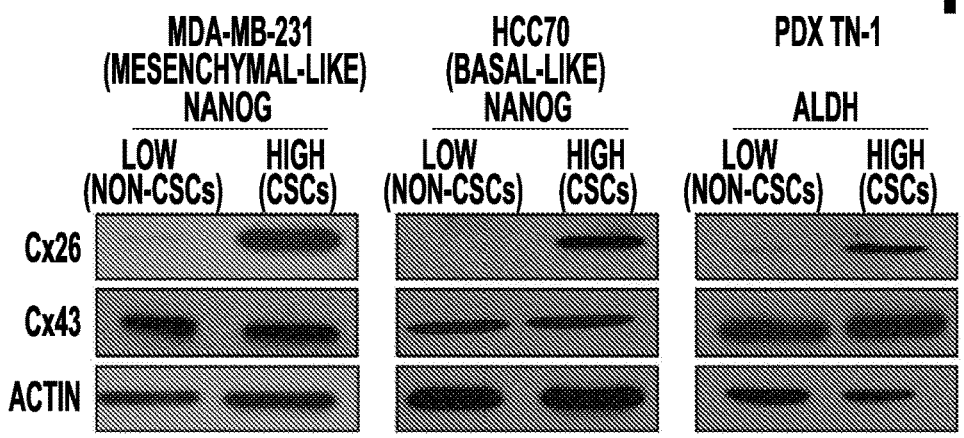
FIGS. 2A-2C provide graphs and images showing Elevated Cx26 expression in TNBC tissue samples and in cancer stem cells enriched from a TNBC cell line and from a patient-derived PDX. (A) Gene expression profiles of 20 different connexins in 2408 TNBC tissue samples were compared with those of normal breast tissue samples across 7 different TNBC-normal datasets using the Oncomine™ (Compendia Bioscience, Ann Arbor, Mich.) database. (B) Cell lysates from MDA-MB-231 NANOG-GFP reporter and PDX TN-1 cells sorted into CSCs and non-CSCs by GFP expression and ALDH activity, respectively, were probed with anti-Cx26 and Cx43 antibodies. Actin was used as a loading control. (C) mRNA expression was determined by qPCR and compared between cancer stem cells (CSCs) and non-CSCs enriched from MDA-MB-231 cells using the NANOG-GFP reporter system and between those enriched from PDX TN-1 cells using ALDH activity sorting (Aldefluor assay). Actin was used as a normalization control (* p<0.05).
Figure 2B:
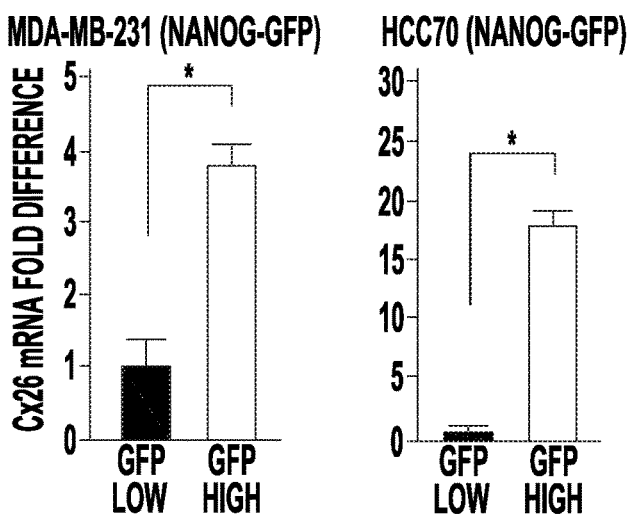
Figure 2C:
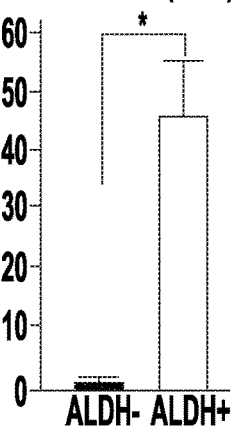

To investigate the role of connexins in the context of their previously reported role as tumor suppressors, 7 different datasets containing a total of 250 normal breast samples and over 2400 TNBC samples were interrogated and it was found that Cx26 was the most highly expressed connexin in TNBC versus non-neoplastic mammary gland tissue (FIG. 2A). This is distinct from the low levels of Cx26 seen in cultured triple-negative MDA-MB-231 breast cancer cells (McLachlan, E. et al., J Membr Biol 218, 107-121 (2007)) and previous observations that some connexins displayed lower expression in breast cancer tissue. Wilgenbus, K. K. et al., Int J Cancer 51, 522-529 (1992). In contrast, Cx43, another connexin that has been well studied in breast cancer, was expressed at similar levels in both normal and TNBC tissue, validating the ranking of the expression levels of connexins using bioinformatics data bases. Given the elevated expression of Cx26 in TNBC tissue and the cellular heterogeneity present within these tumors, whether Cx26 expression was elevated in a specific tumor cell population, including CSCs, was assessed. To address the point, CSC populations were enriched using the previously described CSC reporter system (NANOG promoter-driven GFP) in an established TNBC cell line (Thiagarajan, P.S. et al., Stem Cells 33, 2114-2125 (2015)) and the ALDEFLUOR assay based on aldehyde dehydrogenase (ALDH) activity (Ginestier, C. et al., Cell Stem Cell 1, 555-567 (2007)) in a TNBC patient-derived xenograft (PDX) model. Bry, C. et al., Dev Biol 267, 418-429 (2004). In both models, the CSC-enriched population expressed significantly higher levels of Cx26 mRNA compared with non-CSCs (3.5-fold for the reporter system and 46-fold for the PDX model, FIG. 2C). These differences in CSCs and non-CSCs were further validated at the protein level using immunoblot analysis (FIG. 2B). A similar difference in Cx26 expression was observed between CSC and non-CSC populations in an additional NANOG promoter-driven GFP reporter TNBC cell line (HCC70). As a selectivity control, Cx43 expression in CSCs and non-CSCs was immunoblotted and no difference in expression between CSCs and non-CSCs was observed (FIG. 2B). These results demonstrate that Cx26, but not Cx43, is elevated in TNBC CSCs.

Cx26 is necessary for CSC maintenance.

Figure 3A:
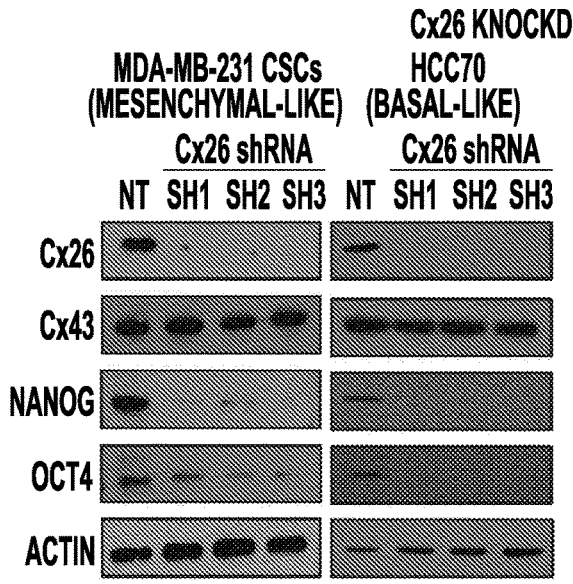
FIGS. 3A-3D provide graphs and images showing Cx26 is necessary and sufficient for maintenance of self-renewal, in vivo tumor initiation and NANOG expression. (A) Cell lysates from MDA-MB-231 CSCs silenced for Cx26 using three Cx26 shRNA constructs (sh1, sh2, and sh3) and a non-targeting shRNA (NT) control were probed with Cx26, Cx43, Oct4, and NANOG antibodies. Actin was used as a loading control. (B) In vivo tumor initiation studies were performed with at least four mice per group, and the p-value was calculated using a log-rank analysis. The graph shows the estimates of stem cell frequencies of NT control compared with the Cx26 sh1, sh2, and sh3 silencing constructs and their corresponding p-values. (C) MDA-MB-231 non-CSCs and HCC70 non-CSCs received Cx26 overexpression vector or empty vector and were probed with anti-Cx26, Oct4, Sox2, and NANOG antibodies. Actin was used as a loading control. (D) In vivo tumor initiation studies were performed comparing the empty vector group with the Cx26 overexpression group, and the p-value was calculated using a log-rank analysis. The graph shows the estimates of stem cell frequencies with the corresponding p-values for the empty vector compared with the Cx26 overexpression in MDA-MB-231 non-CSCs and HCC70 non-CSCs.
Figure 3B:
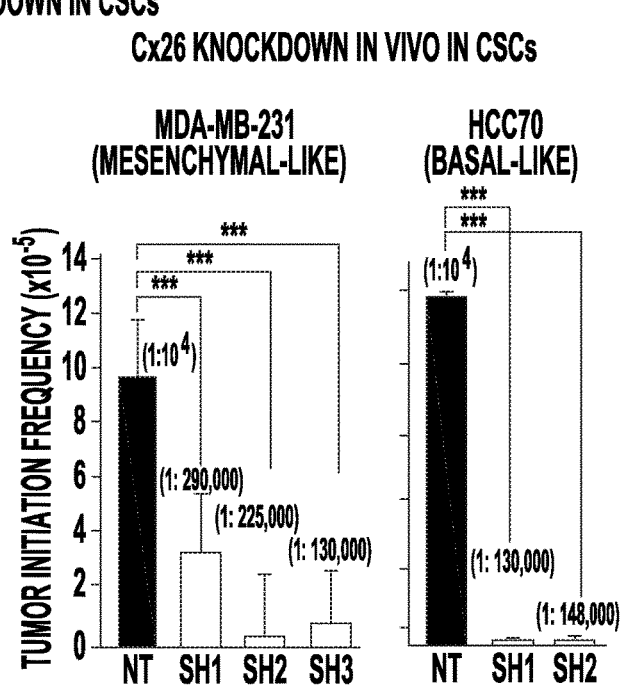

To determine the functional significance of Cx26 in CSCs, a genetic approach to attenuate Cx26 expression was employed. Using three separate non-overlapping Cx26 shRNA silencing constructs, Cx26 protein levels in CSCs was reduced without altering the levels of Cx43, which in other systems may be induced to compensate for the loss of Cx26 (FIG. 3A). Janssen-Timmen, U. et al., Carcinogenesis 7, 1475-1482 (1986). Unexpectedly it was found that Cx26 silencing reduced the expression of NANOG, a key transcription factor important for CSC phenotypes (FIG. 3A). To validate the effect of Cx26 suppression on tumor initiation capacity, Cx26-silenced and control CSCs were injected into immunocompromised mice in a limiting dilution manner It was found that Cx26 silencing significantly reduced tumor-initiating cell frequency from <1 in 10,000 cells in the control group to 1 in 29,000, 1 in 130,000, and 1 in 225,000 cells in each Cx26 silencing condition (FIG. 3B). These data demonstrate that Cx26 is necessary for CSC maintenance and tumor initiation.

Cx26 is sufficient to drive CSC phenotype in non-CSCs.

Figure 3C:
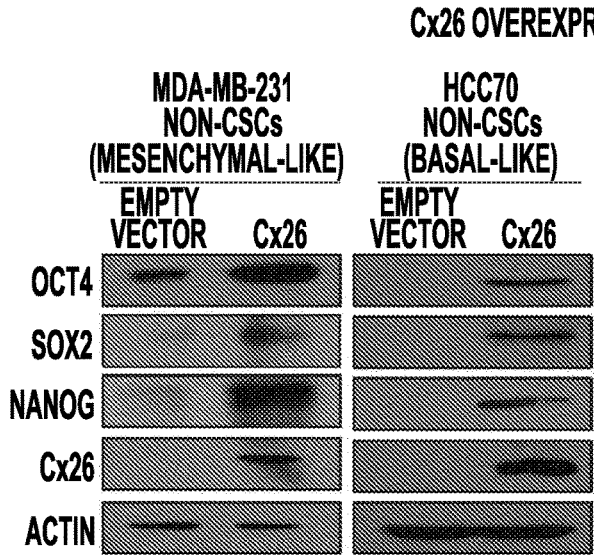
Figure 3D:
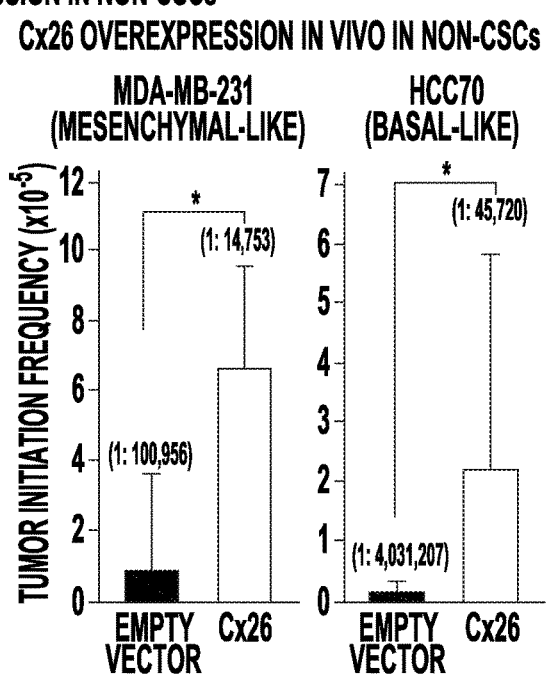

Based on the elevation of Cx26 in CSCs and its necessary role in CSC maintenance, whether Cx26 elevation was sufficient to induce self-renewal capacity in non-CSCs, which express low levels of Cx26, was assessed. A NANOG promoter-driven GFP reporter system that allows for the direct visualization of the stem cell phenotype based on a readout of GFP signal was utilized. Thiagarajan, P. S. et al., Stem Cells 33, 2114-2125 (2015). Cx26 was introduced into MDA-MB-231 and HCC70 GFP-negative non-CSCs (FIG. 3C) and it was found that these cells exhibited an increase in OCT4, SOX2, and NANOG protein expression (FIG. 3C). Similarly, Cx26 overexpression in non-CSCs resulted in significantly elevated tumor initiation frequency, which increased from 1 in 100,956 in the cells transduced with empty vector to 1 in 14,753 in the cells overexpressing Cx26 (FIG. 3D). These data demonstrate that driving Cx26 expression in non-CSCs is sufficient to induce CSC marker expression and increase self-renewal and tumor initiation.

Cx26 is localized in cytoplasmic and nuclear compartments in TNBC.

Based on previous reports showing limited gap junction-dependent coupling in MDA-MB-231 TNBC cells (Qin, H. et al., J Biol Chem 277, 29132-29138 (2002)), whether dye transfer could be detected in the TNBC CSC system was assessed. Using a single-cell microinjection approach (Hitomi, M. et al., Cell reports 11, 1031-1042 (2015)), limited biocytin-rhodamine dye transfer between CSCs was observed, confirming previous results and suggesting that TNBC cells may not utilize connexins for cell-cell communication. Connexins have been shown to possess many channel-independent functions yet have not been extensively explored for Cx26. Vinken, M. et al., Biochimica et biophysica acta 1818, 2002-2008 (2012).

As previous work demonstrated that Cx26 is not localized to the plasma membrane in TNBC cells, determining the localization of Cx26 in the studied cells was desired. Qin, H. et al., Cell Commun Adhes 10, 387-393 (2003). Subcellular fractionation analyses of MDA-MB-231 cells was performed and it was observed that Cx26 was enriched in the post-nuclear cytoplasm fraction (FIG. 4A). While Cx26 was not expressed at a detectable level in the plasma membrane fraction, Cx43 was present at the plasma membrane as expected (FIG. 4A). The localization of Cx26 in MCF7 and MCF10A luminal breast cancer and mammary epithelial cells was further investigated and it was determined that Cx26 was predominantly localized in the isolated plasma membranes of both lines compared with the post-nuclear fraction (FIG. 4B, 4C). To confirm these findings, immunohistological staining for Cx26 in TNBC patient-derived pathological specimens was performed compared to adjacent normal mammary gland tissue. While Cx26 was localized to the plasma membrane in normal mammary epithelium, Cx26 displayed an intracellular localization in three distinct TNBC patient specimens (FIG. 4D). Next immunofluorescence analysis followed by confocal microscopy was performed to visualize the subcellular localization of Cx26. In MDA-MB-231 Cx26 was found in the cytoplasm and associated with the nucleus based on co-staining with lamin B1, a nuclear envelope protein (FIG. 4E). Collectively, these data indicate that in TNBC, Cx26 is not expressed in the plasma membrane where connexins form gap junctions or connexons. These data support a gap junction-independent role of Cx26 that is critical to maintain self-renewal and tumor initiation capacity in TNBC CSCs.

Cx26 is present in a complex containing NANOG and FAK.

Based on the observation that Cx26 silencing decreased NANOG expression in CSCs while Cx26 overexpression increased NANOG expression in non-CSCs, whether there was a direct or indirect link between these two proteins was assessed. As no previously reported direct interaction between Cx26 and NANOG was found, the inventors focused on known connexin interacting partners that also interact with NANOG, and focal adhesion kinase (FAK) emerged as a candidate. Valiente, M. et al., J Neurosci 31, 11678-11691 (2011). FAK is known to interact with Cx26 and, interestingly it also interacts with NANOG outside the nucleus to phosphorylate NANOG. Ho, B. et al., J Biol Chem 287, 18656-18673 (2012). In addition, FAK has been demonstrated to be essential for TNBC CSC maintenance, and FAK auto-phosphorylation at Y397 is an essential event in stem cell self-renewal.

Figure 5A:
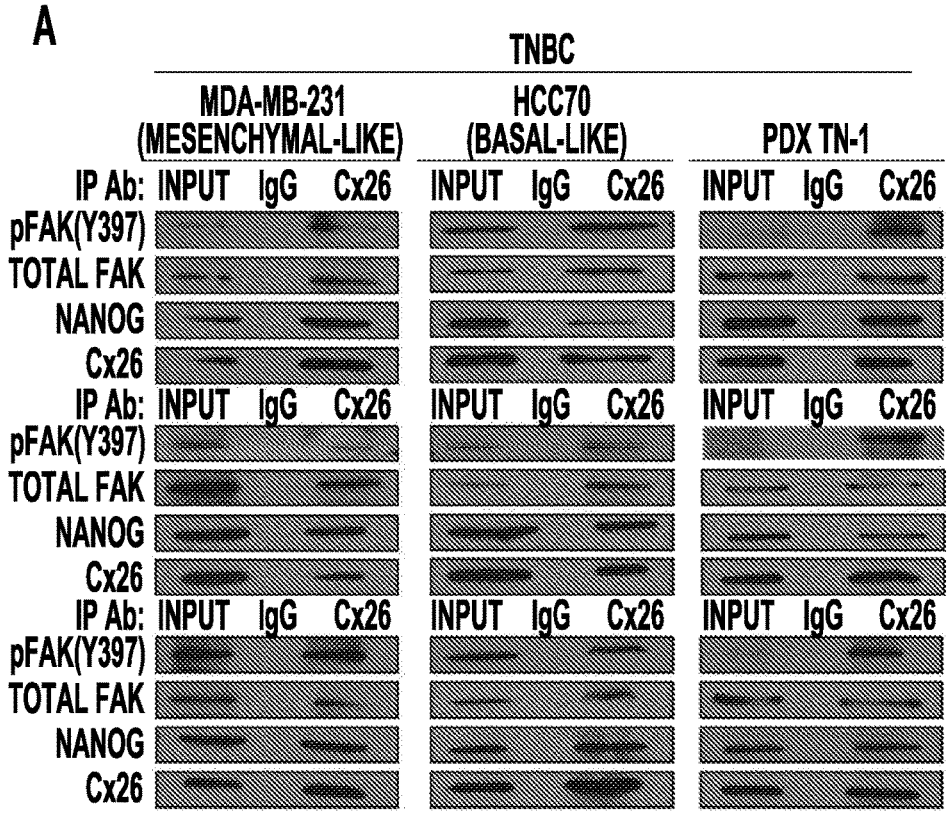
FIGS. 5A and 5C provide graphs and images show that Cx26 forms a complex with focal adhesion kinase (FAK) and NANOG. Cell lysates from bulk cell cultures of (A) MDA-MB-231, PDX TN-1, HCC70, and (B) MCF7 or MCF10A were subjected to immunoprecipitation with anti-Cx26, anti-FAK, and anti-NANOG antibodies and pFAK (Y397), FAK, Cx26, and NANOG proteins in the precipitated complex were detected by western blotting using specific antibodies. Ten percent of the lysate used for immunoprecipitation was loaded as the input control. As a negative control, immunoprecipitation with the corresponding non-immune IgG was performed. (C) Schematic of the interactions detected in TNBC versus normal mammary epithelial and luminal breast cancer cells.
Figure 5B:
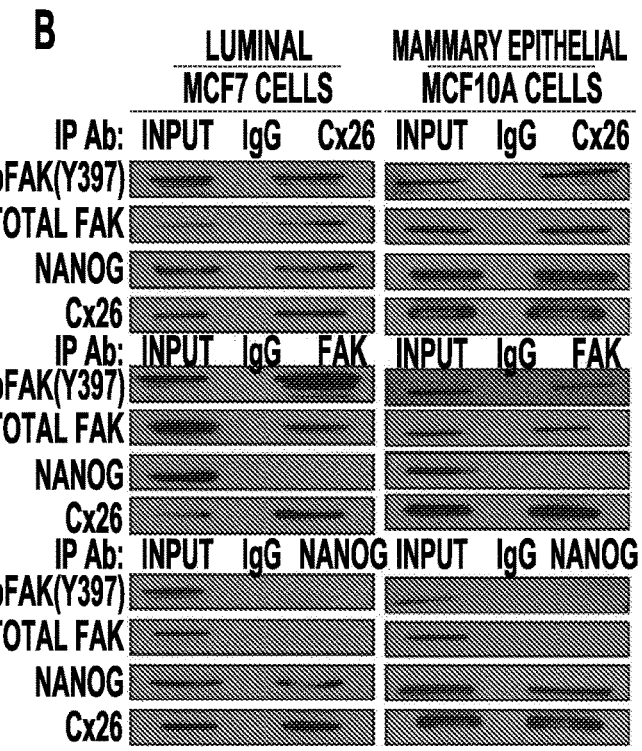
Figure 5C:
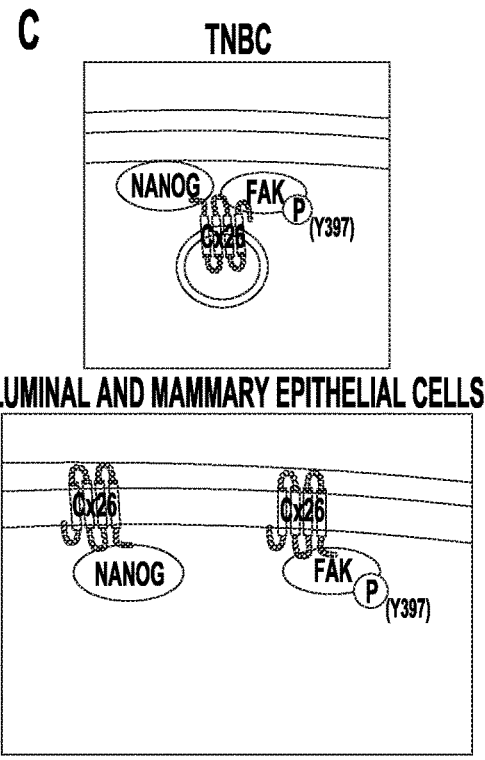

To determine whether Cx26, NANOG, and FAK physically interact, immunoprecipitation studies were performed (FIG. 5A, 5B). TNBC cells (MDA-MB-231, HCC70, and PDX TN-1) were analyzed (FIG. 4A). A luminal breast cancer line (MCF7) and mammary epithelial cells (MCF10A) were also analyzed (FIG. 4B). In all the TNBC lines analyzed, both FAK and NANOG were co-immunoprecipitated with Cx26 (FIG. 5A). To confirm whether these three proteins exist in a complex, immunoprecipitation using a specific antibody against NANOG or FAK was performed and which partners were co-precipitated was examined In TNBC cells, a FAK antibody co-precipitated both Cx26 and NANOG, and a NANOG antibody co-precipitated Cx26 and FAK (FIG. 5A). However, in MCF7 and MCF10A cells, when FAK was immunoprecipitated, NANOG was barely detected, and when NANOG was immunoprecipitated, FAK and pFAK (Y397) were not detected in the immunoprecipitate (FIG. 5A). These data indicate that both NANOG and FAK interact with Cx26 in TNBC cells but that the NANOG/FAK interaction does not occur in MCF7 or MCF10A cells (FIG. 5C). These results establish that both NANOG and FAK interact with Cx26 in TNBC cells.

Next, the role of FAK in the studied cells was investigated by silencing FAK expression in TNBC CSCs or by overexpressing FAK in non-CSCs. FAK silencing in TNBC attenuated self-renewal, confirming previous reports (Luo, M. et al., Cancer Res 69, 466-474 (2009)), while FAK overexpression in non-CSCs induced self-renewal as measured by sphere-formation assays. FAK function is regulated by a series of its own phosphorylation modification, some of which have been linked to self-renewal. Zhao, J. & Guan, J. L., Cancer Metastasis Rev 28, 35-49 (2009). Therefore, FAK phosphorylation status in CSCs and non-CSCs enriched by the NANOG promoter-driven GFP reporter was assessed. Compared with non-CSCs, CSCs contained higher levels of phosphorylation at FAK residue Y397, the autophosphorylation site necessary for self-renewal, while other phosphorylation sites of FAK were not different between the two populations.

Cx26 expression regulates NANOG stability.

Based on the observation that Cx26, NANOG, and FAK interact with each other in TNBC cells, that the Cx26/NANOG/FAK complex was present along with an enrichment of autophosphorylated pFAK (Y397) in MDA-MB-231 CSCs was confirmed (FIG. 6A) In contrast, the ternary complex could not be detected in non-CSCs (FIG. 6B). However, overexpression of Cx26 in non-CSCs was sufficient to drive formation of the complex (FIG. 6B). Moreover, Cx26 overexpression in non-CSCs resulted in a parallel activation of FAK based on autophosphorylation at Y397 (pFAK, FIG. 6B).

To further assess the interaction between Cx26, NANOG, and FAK, the individual components in MDA-MB-231 CSCs were knocked down and the overall expression levels of other members were assessed. Silencing Cx26 in MDA-MB-231 CSCs inhibited NANOG protein expression and FAK autophosphorylation (Y397) but did not affect total FAK levels (FIG. 6C). As Cx26 decreased the protein levels of NANOG, the mechanism of NANOG suppression was examined NANOG mRNA expression was not inhibited in Cx26-silenced MDA-MB-231 CSCs compared to NT controls (FIG. 6D), indicating that post-transcriptional regulation is responsible for the decrease in NANOG protein levels. As a control, Cx26 expression was assessed and it was found that Cx26 mRNA was decreased in Cx26-silenced MDA-MB-231 CSCs compared to NT controls (FIG. 6D). As silencing Cx26 did not alter the NANOG transcript level, whether NANOG protein stability was decreased by blocking protein synthesis with 100 µg/ml cycloheximide was assessed. Cx26-silenced MDA-MB-231 CSCs exhibited a faster decline in NANOG protein levels compared to NT controls (FIG. 6E). These results demonstrate that Cx26 expression is important for maintaining NANOG protein stability.

NANOG silencing decreased the levels of both Cx26 and total FAK in MDA-MB-231 CSCs (FIG. 6F). NANOG regulated Cx26 at the transcriptional level, as shRNA silencing of NANOG led to decreased Cx26 mRNA in MDA-MB-231 CSCs (FIG. 6G). Likewise, NANOG overexpression led to increased Cx26 mRNA in MDA-MB-231 non-CSCs (FIG. 6G). These data support the hypothesis that the members of the Cx26/FAK/NANOG complex can regulate each other, with Cx26 regulating NANOG protein stability and FAK activation.

Next, whether NANOG or FAK could functionally complement the inhibition of sphere initiating frequency in Cx26-silenced cells was tested. In Cx26-silenced MDA-MB-231 CSCs, both NANOG and FAK were able to individually increase sphere initiating frequency, while empty vector did not (FIG. 6H). These rescue studies suggest that NANOG and FAK are able to functionally complement the changes in self-renewal induced by Cx26.

Formation of the Cx26/NANOG/FAK complex is necessary for self-renewal.

Data indicate that Cx26 interacts with NANOG and FAK in a ternary complex that does not localize in the plasma membrane and that the introduction of Cx26 can drive complex formation. To further assess the dynamics of Cx26 introduction on Cx26/NANOG/FAK ternary complex formation, the effect of altering Cx26 localization using two Cx26 loss-of-function point mutants, D66H-Cx26 and G59A-Cx26, was assessed. These mutations have been characterized in the context of sensorineural deafness and hyper-proliferative skin disorders (Maestrini, E. et al., Hum Mol Genet 8, 1237-1243 (1999); Heathcote, K. et al., J Med Genet 37, 50-51 (2000)) and fail to traffic out of the Golgi apparatus, (Thomas, T., et al., J Biol Chem 279, 19157-19168 (2004)) allowing the inventors to test whether mislocalization of Cx26 affects its interaction with NANOG and FAK. When an RFP-tagged version of D66H-Cx26 was introduced into CSCs, the majority of the RFP signal was co-localized with the Golgi apparatus marker GM130, which confirmed its mislocalization. RFP-tagged wild-type Cx26, in contrast, was found both in the Golgi apparatus as well as outside the Golgi apparatus, an expression pattern similar to that of the endogenous Cx26 protein.

Figure 7A:
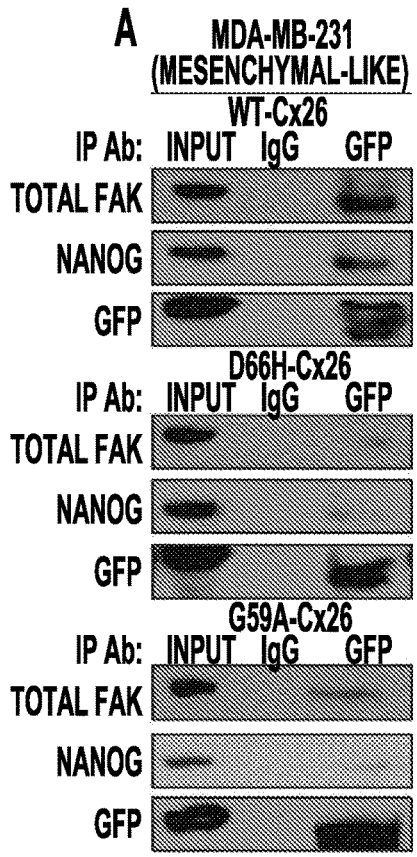
FIGS. 7A-7D provide graphs and images showing the Cx26 mutants fail to complex with FAK/NANOG and disrupt the self-renewal capacity of TNBC CSCs. (A, B) After transfection of plasmids expressing GFP fusion Cx26 wild type and mutant proteins, immunoprecipitation was performed using a GFP antibody in MDA-MB-231 and PDX-TN-1 cells and the resulting immunoprecipitates were probed with FAK, NANOG, and GFP antibodies. (C) Stem cell frequency determined by limiting dilution sphere forming assay indicates that the expression of the D66H-GFP or G59A-GFP mutant Cx26 in MDA-MDMB-231 parental cells significantly reduced CSC frequency compared with the expression of the wild type Cx26-GFP. (D) D66H-RFP Cx26 expression in CSCs reduced CSC frequency compared with the wild-type Cx26-RFP expression in CSCs.
Figure 7B:
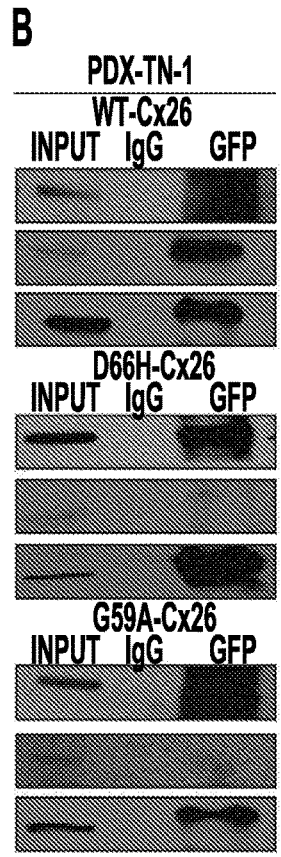
Figure 7C:
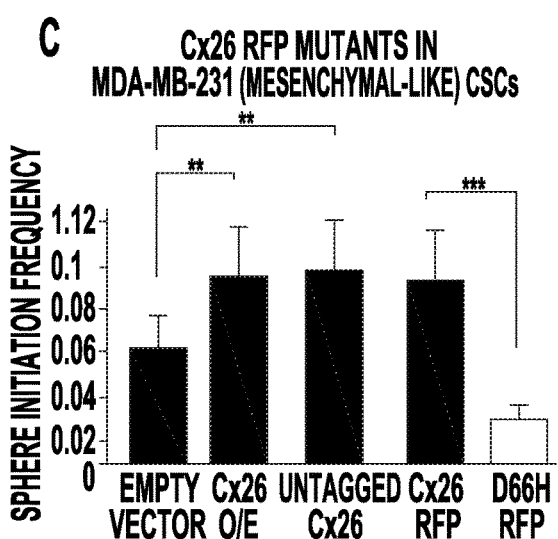
Figure 7D:
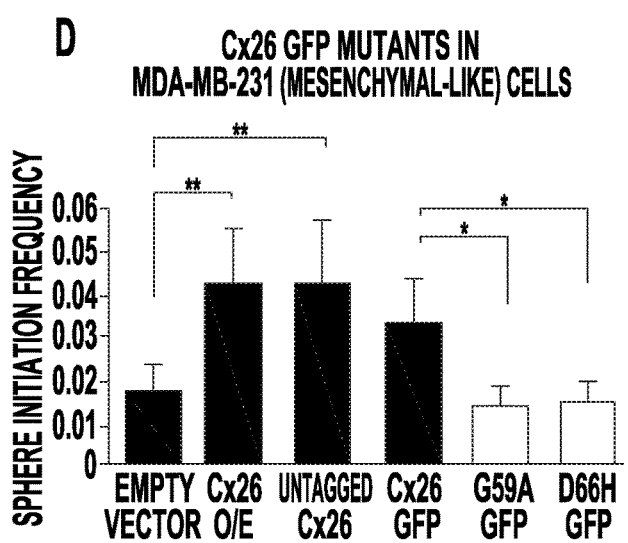
Figure 8:
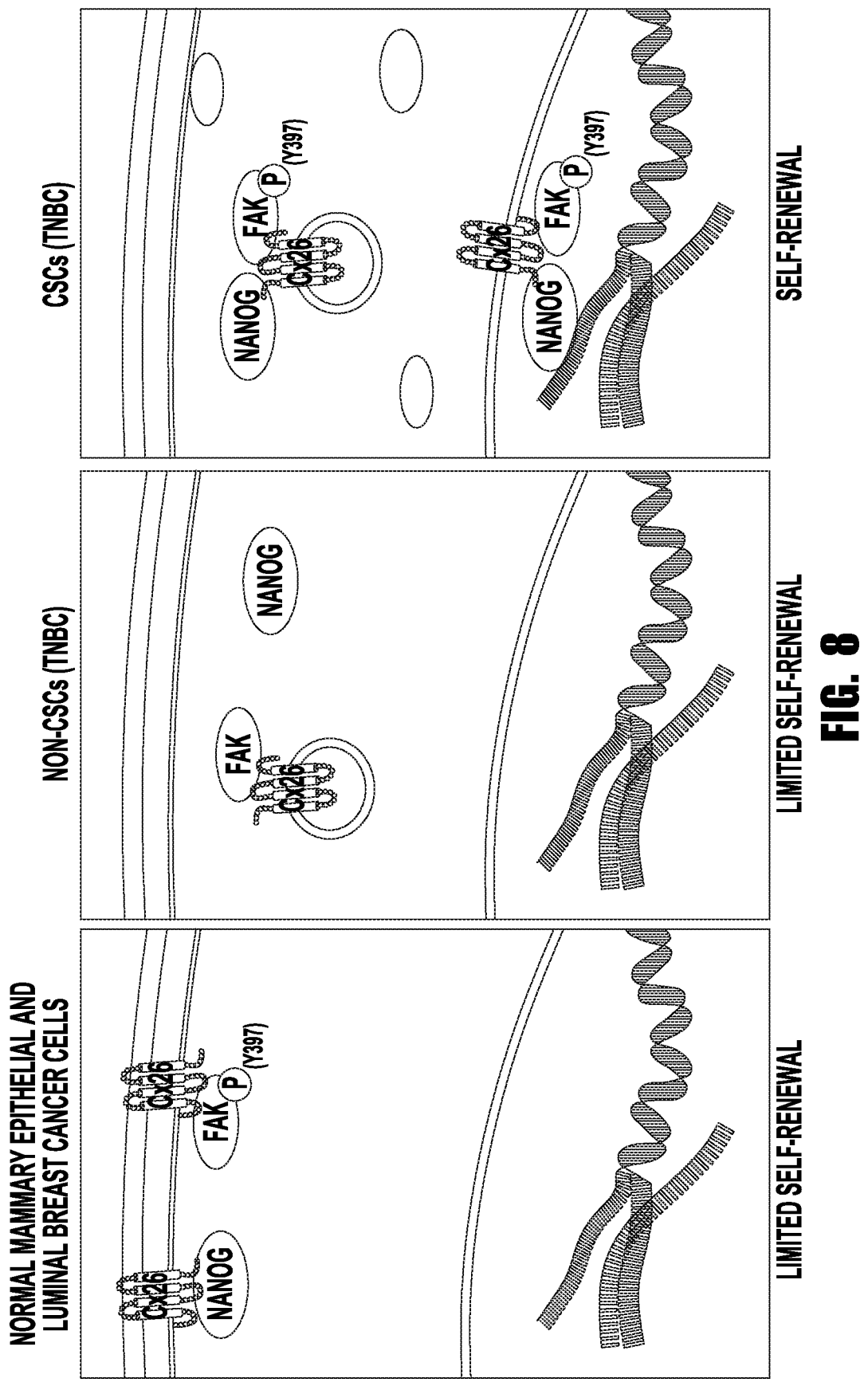
FIG. 8 provides images showing a model of Cx26, NANOG, and FAK interaction in luminal breast cancer and TNBC. In luminal breast cancer cells, Cx26 interacts with FAK and NANOG individually, but the Cx26/NANOG/FAK complex does not form. In TNBC non-CSCs, FAK interacts with Cx26 but is not phosphorylated and NANOG is not present in a complex with Cx26 and FAK. In TNBC CSCs, all three proteins are expressed and form a complex, driving self-renewal.

To analyze the ability of each Cx26 mutant to complex with FAK and NANOG, GFP-tagged versions of wild-type, G59A, or D66H mutant Cx26 were introduced into cells. For these analyses, parental MDA-MB-231 cells expressing no GFP were used. When wild-type Cx26 was introduced into MDA-MB-231 cells and immunoprecipitated using a GFP antibody, NANOG and FAK were detected as expected (FIG. 7A), and this observation was reproduced in PDX cells (FIG. 7B). However, when the mutants were introduced into MDA-MB-231 or PDX cells and immunoprecipitated using a GFP antibody, NANOG was not detected indicating a lack of association with the Cx26 complex (FIG. 7A, B), and demonstrating that mislocalized Cx26 has a limited ability to form the ternary complex. Finally, the biological consequences of the mislocalized Cx26 mutants that were unable to form the ternary complex were assessed. When these Cx26 mutants were introduced into MDA-MB-231 cells or into CSCs, reduced sphere initiation frequency (1 in 19.8 for empty vector, 1 in 11.8 for Cx26 overexpression, 1 in 11.5 for untagged Cx26, 1 in 12.1 for Cx26-RFP, and 1 in 53.8 for D66H-RFP, FIG. 7C) was observed, indicating that self-renewal was disrupted (FIG. 7C). Further, when Cx26 D66H and G59A mutants were introduced into MDA-MB-231 parental cells, sphere initiation frequency was not enhanced compared to introduction of WT Cx26 (1 in 63 for empty vector, 1 in 24.5 for Cx26 overexpression, 1 in 24.1 for untagged Cx26, 1 in 31.6 for Cx26-GFP, 1 in 78.4 for G59A-GFP, and 1 in 77.8 for D66H-GFP, FIG. 7D). Collectively, these data indicate that Cx26 mutations suppress NANOG binding activity and also abrogate the ability of Cx26 to promote sphere formation, highlighting the critical role of Cx26 in the formation of a ternary complex that promotes CSC maintenance (FIG. 8).

Discussion

These studies define a new gap junction-independent role for Cx26 in the maintenance of CSC self-renewal in TNBC. Connexins are predominantly considered tumor suppressors in many solid cancer models (Naus, C. C. & Laird, D. W., Nature reviews. Cancer 10, 435-441 (2010)), however recent studies challenge this paradigm, as connexins appear to modulate invasion and metastasis, indicating that they are only conditional tumor suppressors. The inventors demonstrate that Cx26 is present in a ternary complex with FAK and NANOG in the cytoplasm and the nucleus. Moreover, FAK activation and NANOG stability are dependent on Cx26 in TNBC. This complex is specific to TNBC, as NANOG and FAK do not co-immunoprecipitate in mammary epithelial and luminal breast cancer cells. Complex formation with Cx26 may provide a scaffold for the NANOG/FAK interaction that is critical for self-renewal specifically in TNBC.

Self-renewal programs ensure the maintenance of a reservoir of stem cells that can give rise to differentiated progeny. Intrinsic programs and extrinsic factors (such as mitogens and cell-cell interactions) play pivotal roles in determining the fate of CSCs (self-renewal versus differentiation). It is observed that NANOG and FAK, two intrinsic factors that are critical for breast CSCs, physically interact with Cx26 and that the expression of Cx26 was essential for Y397 phosphorylation of FAK and the stability of NANOG. These data suggest that Cx26 serves as a critical signaling hub via its interaction with NANOG and FAK. Tate, A. W. et al., Prostate 66, 19-31 (2006). There is building evidence that the NANOG signaling network is expansive and interacts with proteins that have functions beyond stem cell maintenance. NANOG downstream regulation is relatively well characterized and emerging evidence suggests that NANOG can interact with other proteins such as Bmi1 and numb via aurora A kinase and atypical PKC zeta to promote self-renewal and tumorigenesis. Xie, X. et al., Oncogene 33, 2040-2052 (2014). The regulation of NANOG expression itself in cancer requires a more in depth understanding. In embryonic stem cells, NANOG degradation is regulated by a motif rich in proline, glutamine, serine and threonine and NANOG protein stability has been described to require interaction with developmental pluripotency associated 5 (DPPAS) or Pin1 via NANOG phosphorylation. The inventors' findings suggest that the NANOG signaling network can be influences by connexins in a gap junction-independent manner that results in stabilization of NANOG. Likewise, the role of FAK has expanded beyond its well-established function in cell adhesion. For example, FAK directly phosphorylates NANOG to promote cell survival and to induce self renewal. Golubovskaya, V. M., Anticancer Agents Med Chem 13, 576-580 (2013).

Breast cancer has served as an experimental paradigm for molecular analysis and characterization of CSCs, representing the first tumor to be subclassified and serving as a precursor to The Cancer Genome Atlas efforts and the first solid tumor found to contain CSCs. CSCs represent a barrier to the development of more effective TNBC therapies. Recent single-cell data from primary breast tumors indicate that cell lines can be used as relevant model systems to interrogate the functions of CSCs, as high similarities between cell lines and primary breast cancer samples have been observed. 68. Akrap, N. et al., Stem Cell Reports 6, 121-136 (2016). This further strengthens the inventors' findings in using the TNBC CSC reporter system and the relevance of this system for revealing a novel interaction between Cx26, NANOG, and FAK that may be amenable for clinical targeting. Despite its importance in self-renewal, targeting NANOG for therapeutic purpose remains difficult as it is a transcription factor. FAK, on the other hand, can be a candidate for targeting because FAK inhibitors have been developed and are currently being evaluated in the context of tumor initiation, growth, and metastasis. However, FAK is essential in numerous normal cellular processes, and while FAK inhibition may alter NANOG activity, it is likely to be associated with adverse clinical complications. The current study suggests that targeting Cx26 may be an effective alternative to targeting both FAK and NANOG as modulating Cx26 expression and function disrupt critical ternary Cx26/NANOG/FAK complex that is vital for non TNBC tumorigenicity. Furthermore, inhibiting Cx26 may have an effect on metastatic disease, as Cx26 has been shown to enhance metastasis, likely by promoting lymphatic vessel invasion. Targeting Cx26 may have less adverse complications than FAK targeting because, Cx26 is essential for normal mammary epithelium during early pregnancy but is not essential for normal mammary cell function. Stewart, M. K. et al., PLoS One 9, e101546 (2014). However, adverse effect on cochlear hair cell must be carefully examined. Cx26 might be clinically useful as a new prognostic factor informative of TNBC patient outcome. Taken together, these studies reveal a unique signaling complex containing Cx26, NANOG, and FAK that may be amenable for targeting and compromising TNBC CSC maintenance.

Experimental Procedures

Cell Culture

MDA-MB-231, MCF10A, MCF7 and HCC70 breast cancer cells and HEK293T cells (American Type Culture Collection; Manassas, Va.) were cultured in log-growth phase in modified Eagle's medium (MEM)/DMEM/F12 medium (MCF10A) supplemented with 1 mM sodium pyruvate (Cellgro, Kansas City, Mo.) and 10% heat-inactivated fetal calf serum (FCS) at 37° C. in a humidified atmosphere (5% $CO_2$). Triple-negative patient-derived xenograft (PDX) TN-1 cells were procured and transduced with dTomato as previously described. Bry, C. et al., Dev Biol 267, 418-429 (2004).

Bioinformatics

The OncomineTM bioinformatics platform was used to mine human breast cancer microarray data comparing the expression of connexins including Cx26 in 7 different TNBC (2408 patient samples) datasets with normal breast tissue (250 samples). The respective genes were entered into the database to obtain Kaplan-Meier survival plots in which the number at risk is indicated below the main plot. Hazard ratio (HR; and 95% confidence intervals) and log rank p were calculated and displayed on the webpage.

Immunohistochemical Staining

The Human Protein Atlas (available online) was used to study the protein expression of Cx26 and Cx43 in normal breast and TNBC tissue samples. Uhlen, M. et al., Mol Cell Proteomics 4, 1920-1932 (2005).

Immunoblotting

Cells were lysed, and protein concentrations were measured using Bradford reagent (BIO-RAD, Hercules, Calif.). Lysates (20 µg total protein) were resolved by 10% SDS-PAGE and electrotransferred to PVDF membrane. After blocking membranes were incubated overnight at 4° C. with primary antibodies against Cx26 (Invitrogen, Grand Island, N.Y.), Cx43 (Cell Signaling, Danvers, Mass.), NANOG (Cell Signaling, Danvers, Mass.), GFP (Invitrogen, Grand Island, N.Y.), SOX2 (Cell Signaling, Danvers, Mass.), OCT4 (Cell Signaling, Danvers, Mass.), phospho-FAK (Y397, Y576, Y925) (Cell Signaling, Danvers, Mass.), total FAK (Cell Signaling, Danvers, Mass.), and/or β-actin (Santa Cruz, Dallas, Tex.), followed by incubation with secondary anti-mouse or anti-rabbit IgG antibodies conjugated to horseradish peroxidase (HRP) (Thermo Scientific, Waltham, Mass.). Immunoreactive bands were visualized by exposing films to luminescent signals generated after incubating the membrane with Pierce ECL plus (Thermo Scientific, Waltham, Mass.).

Quantitative Real-Time PCR (qPCR)

qPCR was performed using an ABI 7900HT system with SYBR-Green MasterMix (Qiagen, Valencia, Calif.). Briefly, total RNA was extracted from cells using the RNeasy kit (Qiagen, Valencia, Calif.), and cDNA was synthesized using the Superscript III kit (Invitrogen, Grand Island, N.Y.). For qPCR analysis, the threshold cycle (CT) values for each gene were normalized to expression levels of β-actin. Dissociation curves were evaluated for primer fidelity.

Flow Cytometry for CSC Enrichment

To enrich CSCs, MDA-MB-231 or HCC70 cells transduced for GFP NANOG promoter reporter were subjected to a BD FACS Aria II at a concentration of 1 million cells/mL and sorted according to GFP expression levels with MDA-MB-231 parental cells was used as a control to define negativity for GFP expression. Data analysis was performed using the FlowJo™ software (Tree Star, Inc.).

The ALDEFLUOR kit (StemCell Technologies, Durham, N.C., USA) was also used to isolate the CSC population with high ALDH enzymatic activity. Cells freshly dissociated from the breast cancer PDX TN-1 xenografts were suspended in ALDEFLUOR assay buffer containing ALDH substrate and incubated for 30-60 minutes at 37° C. As a negative control, an aliquot of each sample of cells was treated with diethylaminobenzaldehyde (DEAB), a specific ALDH inhibitor. The sorting gates were established as described in the kit manufacturer's protocol, and cells were sorted into ALDH+ (CSCs) and ALDH− (non-CSCs) accordingly using BD FACS Aria II.

Lentiviral Production and Infection

Lentiviral short hairpin RNAs (shRNAs) and Cx26-transducing lentiviruses were prepared as previously reported. Lathia et al., Cell stem cell 6, 421-432 (2010); Lathia et al., Cell reports 6, 117-129 (2014). 293T cells were cultured in Dulbecco's modified Eagle's medium supplemented with 10% fetal calf serum. 293T cells were co-transfected with the packaging vectors psPAX2 and pMD2.G (Addgene, Cambridge, Mass.) and lentiviral vectors directing expression of shRNA (Sigma, St. Louis, Mo.) specific to GJB2 (TRCN0000059893 (sh1), TRCN0000430109 (sh2), TRCN0000419197 (sh3), TRCN0000059894, TRCN000005895, TRCN0000005896, TRCN000005897, TRCN0000412781, TRCN0000422191), NANOG (TRCN0000004884 (sh1), TRCN0000004885 (sh2), TRCN0000004887, TRCN0000004888), FAK (TRCN0000121127, TRCN0000121209, TRCN0000121319, TRCN0000121207, TRCN0000001617, TRCN0000196310, TRCN0000121318, TRCN0000194984, TRCN0000121129, TRCN0000001620), a non-targeting control (NT) shRNA (SHC002), and overexpression vector for GJB2 (Cx26) or an empty vector (Applied Biological Materials, Richmond, BC, Canada). Media of the 293T cultures were changed 18 hours after transfection, and viral particles were harvested at 48 and 72 hours, concentrated with polyethylene glycol precipitation, and stored at −80° C. for future use. Viral infections were carried out in MDA- MB231 parental cells, CSCs and non-CSCs. Transduced cells were selected by their resistance to 2 µg/mL puromycin.

Stability Assays

MDA-MB-231 CSCs with or without Cx26 silencing were treated with cycloheximide (CHX) at a concentration of 100 µg/mL following 24-hour puromycin selection. Non-target and shRNA-silenced cells were subsequently harvested at different time intervals. Equal amount of protein from the non-target and the three non-overlapping Cx26 shRNA-treated constructs were analyzed by probing for NANOG by immunoblotting.

Limiting Dilution Assays

For tumor-sphere formation assays, cells were cultured in duplicate rows of serial dilutions per well in a 96-well plate (Sarsted, Germany) per condition with 200 µl serum-free DMEM/F12 medium supplemented with 20 ng/ml basic fibroblast growth factor (Invitrogen, Grand Island, N.Y.), 10 ng/ml epidermal growth factor (BioSource, Grand Island, N.Y., USA), 2% B27 (vol/vol) (Invitrogen, Grand Island, N.Y.), 10 µg/ml insulin, and 1 µg/ml hydrochloride (Sigma, St. Louis, Mo.). Tumorsphere formation was scored after 2 weeks under a phase contrast microscope. The frequency of sphere forming cell was calculated accordingly using an extreme limiting dilution algorithm (ELDA). Hu, Y. & Smyth, G. K., J. Immunol Methods, 347, 70-78 (2009).

In Vivo Tumor Formation

NOD SCID gamma (NSG) mice were purchased from the Biological Resource Unit (BRU) at the Cleveland Clinic. All mice were maintained in micro isolator units with free access to food and water. All mouse procedures were performed with adherence to protocols approved by the Institute Animal Care and Use Committee at the Lerner Research Institute of the Cleveland Clinic.

Cx26-silenced and non-target (NT) control MDA-MB-231 CSCs were subcutaneously transplanted into the right flank of female mice at 6 weeks of age in serial dilutions of 8000, 80,000, and 800,000 cells per injection. Injections of MDA-MB-231 non-CSCs overexpressing Cx26 or empty vector were also conducted as described above. Mice were monitored every day until the endpoint of day 40. Palpable tumors with a cross-sectional area >2 mm$^2$ were taken as a positive read for tumor formation. The stem cell frequencies were calculated using an extreme limiting dilution algorithm (ELDA).

Immunoprecipitation

Immunoprecipitation was performed by incubating the cell lysates with the indicated antibodies and the corresponding control antibodies overnight at 4° C. Protein A/G agarose beads (Santa Cruz, Dallas, Tex.) were washed 3-4 times at 4° C. The washed beads were incubated with the antibody/lysate mix for 2 hours at 4° C. The beads were then washed 3-4 times at 4° C. Laemmli sample buffer was then added to the beads and boiled for 5 minutes. Immunoblotting was performed using the supernatants as described above.

Transfection of Cx26 Expression Plasmids

MDA-MB-231 parental cells, NANOG-GFP and PDX TN-1 cells were transfected with the RFP- or GFP-tagged wild-type or mutant Cx26 expression plasmids (Thomas, T. et al., J Biol Chem 279, 1915719168 (2004)) using X-treme-GENE HP DNA Transfection reagent (Roche, Indianapolis, Ind.) according to the manufacturer's protocol. The transfected cells were identified based on their RFP or GFP fluorescence. These cells were used for fluorescence microscopy to determine subcellular localization of fusion Cx26 protein and also for immunoprecipitation for pull down using anti GFP antibody.

Immunofluorescence Microscopy

To visualize the expression and localization of Cx26 and FAK in MDA-MB-231 and HCC70 parental cells and CSCs, the cells were plated on a coverslip placed in a 6-well plate. Cells were fixed with 4% paraformaldehyde for 15 minutes and washed three times with PBS containing 0.1% Triton X-100 for 5 minutes each. After washing, cells were permeabilized and blocked in 5% FBS with 0.1% Triton X-100 in 1× PBS for 1 hour. Primary antibodies (Cx26, FAK, Calnexin, and GM130) and AF-647-labelled phalloidin were used to stain cells overnight at 4° C. The following day, cells were washed three times with PBS for 5 minutes each, and the appropriate secondary antibody was applied for 1 hr at room temperature. After secondary antibody incubation, cells were washed three times with PBS for 5 minutes each and counterstained with 4',6-diamidino-2-phenylindole (DAPI) for 5 minutes. Afterwards, cells were washed three times with PBS for 5 minutes each. The coverslips were mounted using FluorSave Reagent (VWR International, Radnor, Pa.). Cells were imaged using a confocal microscope, and images were prepared in using Adobe Photoshop.

Subcellular Fractionation

In order to separate a fraction of plasma membrane and a fraction of post-nuclear cytosol and organelles, cells were grown in 15 cm dishes to 90-100% confluence. Cells were then placed on ice, the media was aspirated, and cells were scraped in 3 mL of ice-cold buffer (250 mM sucrose, 1 mM EDTA, 20 mM tricine, pH 7.8). Cells were pelleted by centrifugation at 1400×g for 5 minutes. The pellet was resuspended in 1 mL of the buffer and homogenized using a Dounce-type homogenizer. The post-nuclear supernatant (PNS) was removed and stored on ice. The pellet was resuspended in 1 mL of the buffer, homogenized, and centrifuged at 1000×g for 10 minutes. The two PNS fractions were combined and layered on top of 30% Percoll (Sigma, St. Louis, Mo.) in the buffer and centrifuged at 84,000×g for 30 minutes at 4° C. The observed visible band of plasma membrane and the cytosol and organelle fraction were collected and diluted with the buffer. The plasma membrane fraction was centrifuged at 105,000×g for 90 minutes to remove the Percoll. The membrane fraction was resuspended in the buffer with protease and phosphatase inhibitors. The samples were then immunoblotted with the indicated antibodies.

To obtained nuclear and cytoplasmic fractions, the following procedure was used. Cytoplasmic extraction from pelleted cells were performed by resuspension in cytoplasmic extraction buffer (HEPES (10 mM, pH 7.9), NaCl (50 mM), Sucrose (0.5 M), EDTA (0.1 mM), EGTA (0.1 mM), Triton X-100 (0.5%), DTT (1 mM)). The lysates were centrifuged at 20000×g for for 5 minutes at 4° C. The supernatants were saved as the cytoplasmic fraction. The pellets were washed in phosphate-buffered saline twice followed by extraction of the nucleus by using nuclear extraction buffer (HEPES (10 mM, pH 7.9), KCl (10 mM), EDTA (0.1 mM), EGTA (0.1 mM), DTT (1 mM)). The resuspended pellets were centrifuged at 20000×g for for 10 minutes at 4° C. The supernatants were saved as the nuclear fraction.

Gap Junction Dye Diffusion Assay

To quantify gap junction-mediated intercellular diffusion, a microinjection-based analysis in MDA-MB-231 CSCs was performed as described previously. Hitomi, M. et al., Cell reports 11, 1031-1042 (2015). MDA-MB-231 CSCs were plated on coverslips at subconfluent density the day before the assay. A single cell within a cell cluster was co-injected with biocytin-rhodamine together with Cy5-labeled IgG Immediately after microinjection, time-lapse video microscopy was used to capture phase contrast, red (for biocytin-rhodamine), and far-red (for Cy5 IgG) fluorescent images. The Cy5 IgG image defines the initially injected donor cells, and the red signal outside of this donor cell is the dye diffused out of the donor cells into the neighboring cells when gap junction is functional.

Statistical Analysis

Values reported in the results are mean values +/− standard deviation. One-way ANOVA was used to calculate statistical significance, and the p-values are detailed in the text and figure legends.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A peptide having a size of 50 amino acids or less comprising a fragment of Cx26 comprising an amino acid sequence having at least 95% identity and only conservative substitutions to SEQ ID NO: 3 or SEQ ID NO: 5 and a protein transduction domain.

2. The peptide of claim 1, wherein the peptide comprises an amino acid sequence, having at least 95% identity and only conservative substitutions to SEQ ID NO: 3.

3. The peptide of claim 1, wherein the peptide comprises an amino acid sequence having at least 95% identity and only conservative substitutions to SEQ ID NO: 5.

4. The peptide of claim 1, wherein the protein transduction domain is derived from *Antennapedia*.

5. The peptide of claim 3, wherein the peptide comprises an amino acid sequence having at least 6 amino acids selected from the group consisting of SEQ ID NO: 20 and SEQ ID NO: 21.

6. A method of treating triple negative breast cancer in a subject in need thereof, comprising administering to the subject a therapeutically effective amount of a peptide of claim 1.

* * * * *